(12) United States Patent
Palepu

(10) Patent No.: US 12,048,708 B2
(45) Date of Patent: *Jul. 30, 2024

(54) IN-VIAL DEPOSITION OF A STABLE, STERILE AND CRYSTALLINE O-ACETYL SALICYLIC ACID (ASPIRIN)

(71) Applicant: RHOSHAN PHARMACEUTICALS, INC., Glen Mills, PA (US)

(72) Inventor: Nagesh R Palepu, Southampton, PA (US)

(73) Assignee: RHOSHAN PHARMACEUTICALS, INC., Glen Mills, PA (US)

( * ) Notice: Subject to any disclaimer, the term of this patent is extended or adjusted under 35 U.S.C. 154(b) by 492 days.

This patent is subject to a terminal disclaimer.

(21) Appl. No.: 17/406,285

(22) Filed: Aug. 19, 2021

(65) Prior Publication Data

US 2022/0409636 A1 Dec. 29, 2022

Related U.S. Application Data

(63) Continuation of application No. 16/617,958, filed as application No. PCT/US2018/034866 on May 29, 2018, now Pat. No. 11,096,949.

(60) Provisional application No. 62/512,367, filed on May 30, 2017.

(51) Int. Cl.
| | |
|---|---|
| *A61K 31/616* | (2006.01) |
| *A61K 9/00* | (2006.01) |
| *A61K 9/19* | (2006.01) |
| *A61K 47/26* | (2006.01) |

(52) U.S. Cl.
CPC .......... *A61K 31/616* (2013.01); *A61K 9/0019* (2013.01); *A61K 9/0024* (2013.01); *A61K 9/19* (2013.01); *A61K 47/26* (2013.01)

(58) Field of Classification Search
CPC ........ A61K 31/616; A61K 9/19; A61K 47/26; A61K 47/10; A61K 9/001; A61K 9/0024
See application file for complete search history.

(56) References Cited

U.S. PATENT DOCUMENTS

| | | |
|---|---|---|
| 4,117,603 A | 10/1978 | Smith |
| 4,265,888 A | 5/1981 | Kagitani et al. |
| 4,975,269 A | 12/1990 | Chavkin et al. |

(Continued)

FOREIGN PATENT DOCUMENTS

| | | |
|---|---|---|
| CA | 1131245 A | 9/1982 |
| CN | 104546678 A | 4/2015 |

(Continued)

OTHER PUBLICATIONS

Torrado et al., Characterization of the Physical State of Mannitol after Freeze-Drying: Effect of Acetylsalicyclic Acid as a Second Crystalline Cosolvent, Chem Pharm Bull, 50(5), 567-570. (Year: 2002).*

(Continued)

*Primary Examiner* — Carlos A Azpuru
(74) *Attorney, Agent, or Firm* — LUCAS & MERCANTI, LLP

(57) ABSTRACT

Improved, stable aspirin formulations for intravenous use are disclosed. Methods of lyophilizing the aspirin from bulk solutions as well as kits containing the lyophilized aspirin and methods of treatment using the same are also disclosed.

20 Claims, 5 Drawing Sheets

(56) References Cited

U.S. PATENT DOCUMENTS

| | | | |
|---|---|---|---|
| 5,858,410 A * | 1/1999 | Muller | A61K 9/10 424/494 |
| 6,306,843 B1 | 10/2001 | Burghart et al. | |
| 6,773,724 B2 | 8/2004 | Franckowiak et al. | |
| 7,202,229 B1 | 4/2007 | Finkelstein | |
| 7,449,198 B2 | 11/2008 | Franckowiak et al. | |
| 8,063,243 B2 | 11/2011 | Franckowiak et al. | |
| 8,158,152 B2 | 4/2012 | Palepu | |
| 8,481,600 B2 | 7/2013 | Somberhg et al. | |
| 8,889,902 B2 | 11/2014 | Kalvins et al. | |
| 9,757,529 B2 | 9/2017 | Yadidi | |
| 10,149,823 B2 | 12/2018 | Yadidi | |
| 10,195,147 B1 | 2/2019 | Yadidi | |
| 11,096,949 B2 * | 8/2021 | Palepu | A61K 9/0024 |
| 2002/0091108 A1 | 7/2002 | Franckowiak et al. | |
| 2007/0196364 A1 * | 8/2007 | Krishnamurthy | C07K 16/00 514/11.3 |
| 2008/0096947 A1 | 4/2008 | Opitz et al. | |

FOREIGN PATENT DOCUMENTS

| | | | |
|---|---|---|---|
| CN | 104546680 | A | 4/2015 |
| DE | 202007007241 | U1 | 9/2007 |
| ES | 2189639 | A1 | 7/2003 |
| GB | 912894 | A | 12/1962 |
| GB | 993682 | A | 6/1965 |
| RO | 128007 | A2 | 12/2012 |
| WO | 2000/002565 | * | 1/2000 |
| WO | 2000002565 | A1 | 1/2000 |
| WO | 01/66115 | A2 | 9/2001 |
| WO | 201601066115 | A2 * | 9/2001 |
| WO | 2005039464 | A1 | 5/2005 |
| WO | 2010141711 | A1 | 12/2010 |
| WO | 2014210543 | A1 | 12/2014 |
| WO | 2016139001 | A1 | 9/2016 |

OTHER PUBLICATIONS

Torrado, et al., "Characterization of Physical State of Mannitol After Freeze-Drying . . . ", Chem Pharm Bull., vol. 50, No. 5, pp. 567-570, 2002.

International Search Report and Written Opinion for Corresponding International Application No. PCT/US2018/034866 (11 Pages) (Oct. 1, 2018).

Supplementary European Search Report for Corresponding European Application No. 18808709.2 (Dec. 15, 2020) (7 Pages).

Severine Vessot, et al., A Review on Freeze Drying of Drugs With Tert-Butanol (TBA) + Water Systems: Characteristics, Advantages, Drawbacks, Drying Technology: An International Journal, vol. 30, issue 4, pp. 377-385, 2012.

Examination report for corresponding IN application No. 201947052534, dated Oct. 12, 2020, pp. 1-8.

Dirk L. Teagarden, et al., "Practical Aspects of Lyophilization Using Non-Aqueous Co-Solvent Systems", European Journal of Pharmaceutical Sciences, vol. 15, pp. 115-133, 2002.

Sakchal Wittaya-AreekulL, et al., "Freeze-Drying of Tert-Butyl Alcohol/Water Cosolvent Systems: Effects of Formulation and Process Variables on Residual Solvents", Journal of Pharmaceutical Sciences, vol. 87, No. 4 pp. 491-495, 1998.

Sakchai Wittaya-Areekul, et al., "Freeze-Drying of Tert-Butanol/Water Cosolvent Systems: A Case Report on Formation of a Friable Freeze-Dried Powder of Tobramycin Sulfate", Journal of Pharmaceutical Sciences, vol. 91, No. 4, pp. 1147-1155, 2002.

Rakesh P. Patel., et al., "Formulation, Development and Evaluation of Injectable Formulation of Aspirin", Drugs and Therapy Studies, vol. 3:e2, 7 pages. 2013.

Chitra Telang, et al., "Crystallization of Cephalothin Sodium During Lyophilization From Tert-Butyl Alcohol-Water Cosolvent System", Pharmaceutical Reasearch, vol. 22, No. 1, pp. 153-160, 2005.

Louis Rey, et al., "Freeze Drying/Lyophilization of Pharmaceutical and Biological Products", Drugs and the Pharmaceutical Scinces, vol. 206, pp. 1-580.

International Preliminary Report on Patentability for Corresponding International Application No. PCT/US2018/034866 (8 Pages) (Dec. 3, 2019).

Mark D. Eddleston, et al., "Cocrystallization By Freeze-Drying: Preparation of Novel Multicomponent Crystal Forms", Crystal Growth & Design, vol. 13, No. 10, pp. 4599-4606, 2013.

Office Action from Japanese Patent Office issued on Jun. 14, 2022 in a related Japanese Patent Application No. 2020-517288 and English Translation (8 pages).

Office Action from Chinese Patent Office issued on Sep. 28, 2022 in a related Chinese Patent Application No. 201880036512.X and English Translation (21 pages).

* cited by examiner

12,048,708 B2

IN-VIAL DEPOSITION OF A STABLE, STERILE AND CRYSTALLINE O-ACETYL SALICYLIC ACID (ASPIRIN)

CROSS-REFERENCE TO RELATED APPLICATIONS

This application is a continuation of U.S. Ser. No. 16/617,958 filed Nov. 27, 2019, which is a 371 application of PCT/US2018/034866 filed May 29, 2018 which in turn claims the benefit of priority from U.S. Provisional Application Ser. No. 62/512,367, filed May 30, 2017, the contents of each of which are incorporated herein by reference.

FIELD OF THE INVENTION

The invention is directed stable forms of injectable aspirin, kits containing the same and methods of treatment using the same.

BACKGROUND OF THE INVENTION

Aspirin (o-acetylsalicylic acid, ASA) has been used therapeutically for over 100 years. As a salicylate derivative, it possesses the three properties of non-steroidal anti-inflammatory drugs (NSAIDs): analgesic, anti-pyretic, and anti-inflammatory in treating arthritis, neuralgia and myalgia. In addition to these three properties, Aspirin is also effective in inhibition of platelet aggregation.

The principal therapeutic effect of NSAIDs, such as aspirin, is their ability to inhibit prostaglandin production. Aspirin covalently modifies both COX-1 and COX-2, thus resulting in an irreversible inhibition of cyclooxygenase activity, unlike other NSAIDs that bind to COX reversibly. Inhibition of COX-1 leads to inhibition of platelet aggregation but may also cause irritation of gastric lining and kidney function. Inhibition of COX-2 leads to anti-inflammatory, antipyretic and analgesic actions.

Because of the multiple therapeutic activities of aspirin and salicylic acid (SA), which have included the treatment of mild to moderate pain and fever, reduction in risk of chronic diseases such as thrombotic cardiovascular events and, as suggested by emerging evidence, the reduction in risk of colorectal cancer, aspirin has taken many shapes and sizes. Although aspirin was first synthesized in 1897 and sold as a tablet for many decades, over the past three or four decades various dosage forms that include plain tablets, chewable tablets, effervescent tablets, extended-release tablets, granules and suspensions, fast release/disintegrating tablets, suppositories, powders, creams, and lotions have been introduced.

Aspirin is insoluble in acidic pH as the drug predominantly present in the undissociated form, slightly soluble in water (about 0.3%) and the solubility increases significantly at about pH 5.5 and above. The solubility of aspirin is more than 100 mg/ml at pH 5.5 and above. Aspirin undergoes hydrolytic degradation at all pH conditions to form salicylic acid. The hydrolysis rate is slowest at about pH 2.5. The hydrolytic degradation of aspirin stays the same in the pH region of 4.5 to 8.5. The degradation half-life is about 6 days, which is not adequate to develop a solution formulation of aspirin. The degradation half-life of aspirin is so short, it is even impossible to lyophilize the concentrated bulk solution as 10% of potency loss can be observed in about 1.3 hours. To lyophilize any drug, the bulk solution should not lose any potency for at least 12 hours under ambient conditions. Even at pH 2.5 where hydrolytic degradation of aspirin is slowest, aspirin degrades at the rate of about 2% per day. Poor solutions stability coupled with low solubility does not permit to develop a commercially viable lyophile. Therefore, the development of a solution or lyophilized form of Aspirin injection in aqueous medium is extremely difficult.

Due to such solubility and stability problems with the injectable dosage form, only oral dosage forms of aspirin are being widely used in treating various indications mentioned earlier. However, orally administered aspirin is not completely absorbed and is slow in the onset of pharmacological action. On the other hand, the effectiveness of intravenously administered aspirin solution was said to be four time as high as that of the orally administered equal amount of acetylsalicylic acid.

It was known that this degradation reaction is pH dependent. A lowering of the pH leads to an increased protonation of released lysine, so that it is not available or only available to a very restricted extent for subsequent reaction with O-acetylsalicylic acid.

All attempts to develop a stable injectable formulation of O-acetylsalicylic acid (ASA) have failed despite extensive development efforts over the past five decades. In our opinion, salts of O-acetylsalicylic with amino acid containing two basic groups are unstable due to disproportionation to the constituent parts of the salts. When the salts are dissolved in water, which may be residual, an ionization equilibrium is set up involving the formation of aspirin and the amine salt former. The aqueous solubility of aspirin so formed is very low compared to that of the salt and will tend to precipitate thus causing the equilibrium to replace it but at the same time forming more of the amine salt former. In this way, the solution increases in pH and becomes more unstable. Higher pH conditions result in amidolysis of O-acetylsalicylic acid to form amino acid derivative of O-acetylsalicylic acid as well as O-salicylic acid. The presence of such impurities in the injectable formulation of aspirin is not desirable.

Since its discovery of aspirin in 1859, and later worldwide commercialization by Bayer in 1899, O-acetylsalicylic acid (ASA, aspirin; Aspirin® is registered trademark of Bayer) has been a medical mainstay drug for the treatment of pain, fever, inflammation, and inhibition of platelet aggregation in the setting of thrombus (clots).

Aspirin is the only common small molecule drug which also possesses the unique ability to inhibit the aggregation of platelets in the blood, and thus prevent, reduce or eliminate platelet-related clots in blood vessels, tissues and vital organs. Aspirin is only available as an oral tablet or capsule, requiring ingestion by mouth and subsequent absorption in the stomach and GI tract, with onset of inhibition of platelet aggregation occurring from approximately 40 minutes following oral dosing.

When treating platelet-related thrombosis in the setting of heart attack or stroke, minutes count to save lives. Oral tablet aspirin given in the ambulance or ER does not have an immediate effect, relative to rapid-onset of IV infusion clot-busting drugs such as TPA, low-molecular weight heparin and glycoprotein IIb/IIIa inhibitors.

Hundreds of millions of people experience acute (sudden onset) pain, in the settings of headache, migraines, arthritis, musculoskeletal or skin trauma, fractures, dental and surgical wound pain, and from complications of cancer and diabetes. Most analgesic pain medications, including aspirin, are available as oral tablets and take about 30 minutes for initial onset of pain relief. Opioid pain medications are now available as fast-acting and slow-release dosage forms and take about 30 minutes for initial onset of pain relief. However, opioids are widely known to be highly-addictive, and can cause cardio-respiratory distress with standard- or over-dosages.

Thus, the quest continues for a highly-effective, "rapid-onset", predictable and tolerable agent for inhibition of platelet-related thrombosis, and a non-addicting drug for the treatment of acute pain, fever, inflammation. Thus, there exist a critical medical need for a parenteral dosage form of aspirin which provides immediate therapeutic action in acute coronary syndrome and other vascular indications.

SUMMARY OF THE INVENTION

In one aspect of the invention there is provided a liquid aspirin-containing composition having enhanced stability. The composition of the bulk solutions includes aspirin and a cosolvent containing an organic solvent and water. The ratio of the organic solvent to the water is from about 95/5 to 50/50.

In another aspect of the invention there is provided the use of the liquid aspirin-containing compositions as a bulk solution for preparing lyophilized aspirin. A still further aspect of the invention includes methods of preparing lyophilized aspirin. The methods include providing the liquid aspirin containing compositions described herein, lyophilizing the compositions and recovering the resultant lyophilized aspirin. The liquid aspirin containing compositions can contain from about 20 to about 100 mg/ml of aspirin and the cosolvent can include t-butyl alcohol and water. Lyophilized aspirin prepared by the process described herein is also an aspect of the invention. Such lyophilized aspirin having shelf life of at least 2 years under ambient storage conditions.

Still further aspects of the invention include kits for aspirin therapy comprising a first container comprising a therapeutic amount of lyophilized aspirin and a second container comprising water, and a basifying agent and optionally a surfactant such as polysorbate 80. Suitable basifying agents include amino acids or organic bases and inorganic bases or basic salts of alkaline and alkali metals which have a pKa is 8.5 or greater. The amount of the basifying agent is an amount sufficient to provide the solution resulting from combining the contents of the first and second containers with a pH of at least about 5.5 and preferably 6.0 or near physiological pH.

Another aspect of the invention is an intravenously-injectable liquid aspirin-containing composition prepared by combining the contents of the first and second containers in the kit described herein. Methods of providing aspirin therapy, comprising: intravenously administering an effective amount of the liquid intravenously-injectable aspirin-containing compositions described herein to a mammal in need thereof.

DETAILED DESCRIPTION OF THE INVENTION

Figure 1A:
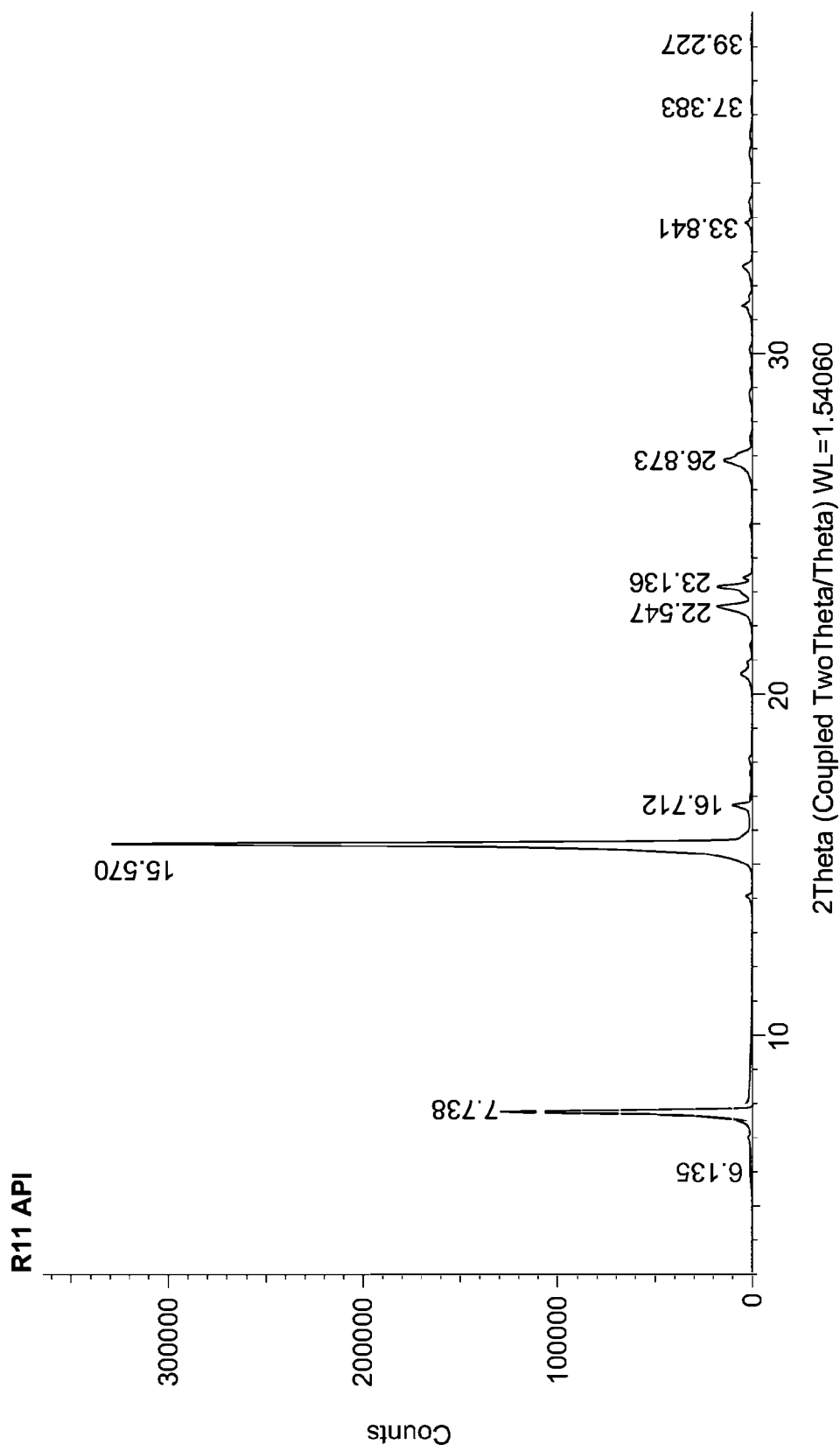
FIGS. 1a, 1b, 1c and 1d are X-ray diffractograms of aspirin API, and lyophile made with different concentrations in accordance with the invention and Example 18.
Figure 1B:
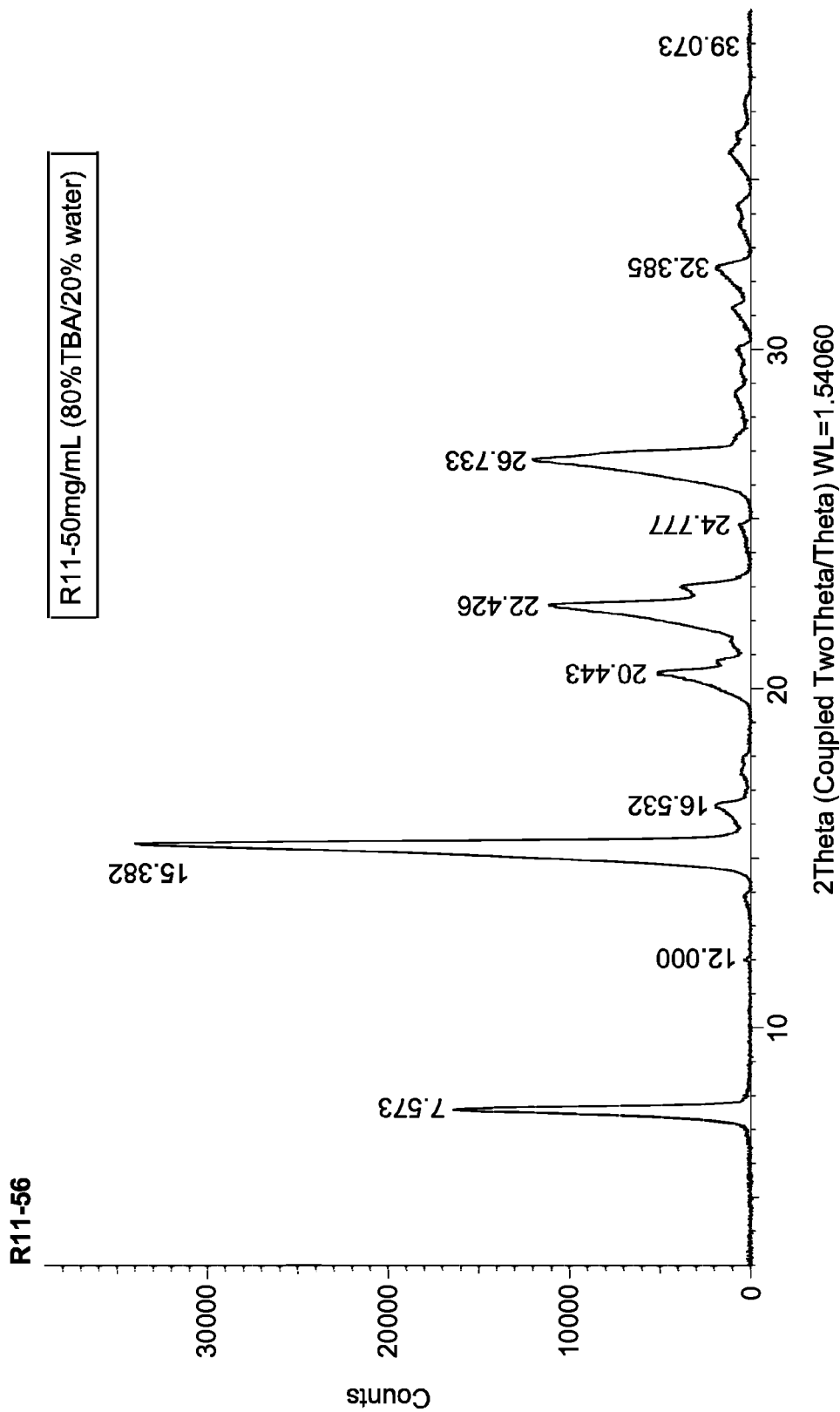
Figure 1C:
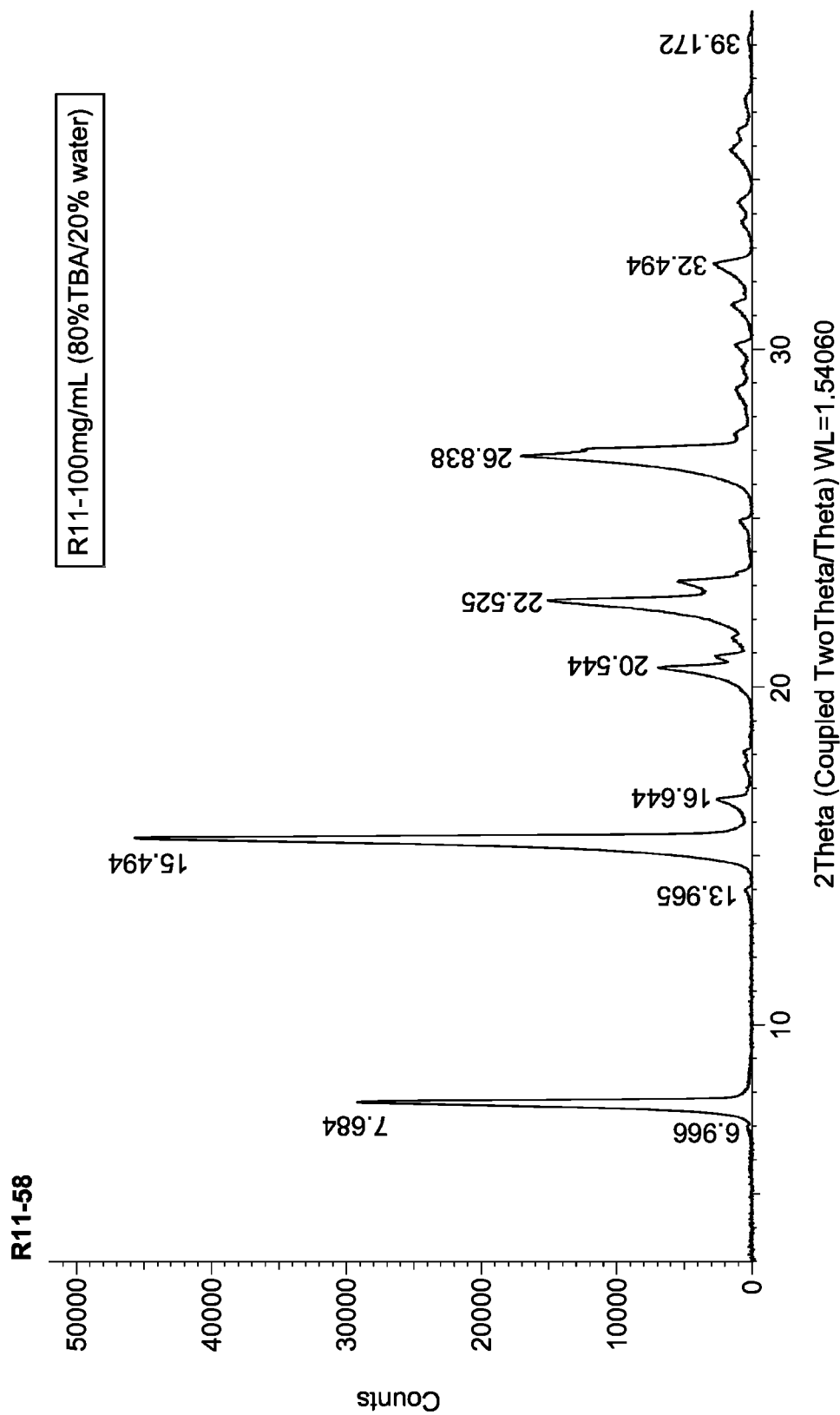
Figure 1D:
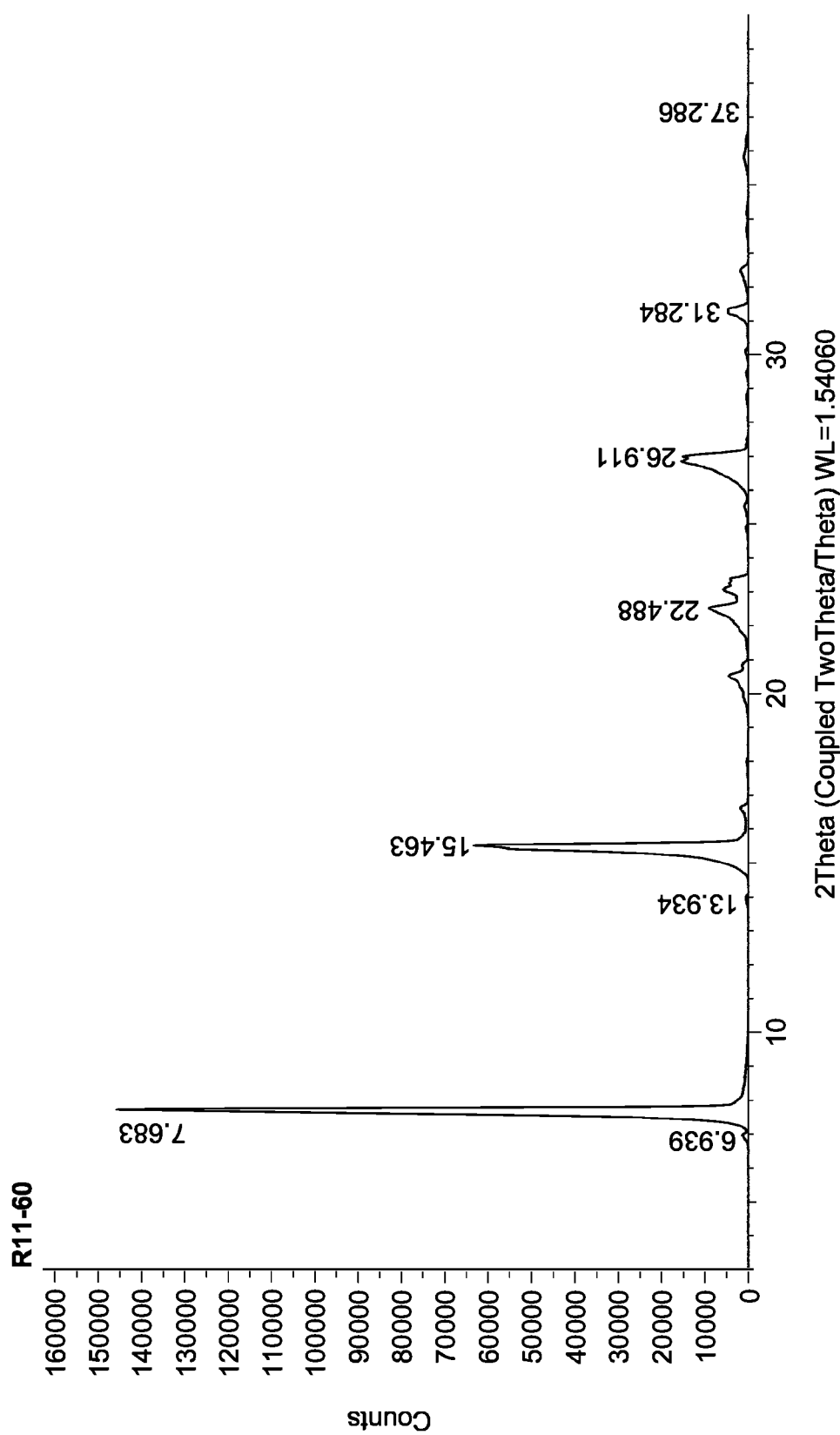

The aqueous solubility of aspirin is about 3 mg/ml. This concentration is quite low to administer an adequate dose of aspirin. For example, to administer 100 mg about 33.3 ml of aspirin solution need to be administered. The volume is large to administer as a bolus injection. The diluted solution must be administered as a rapid infusion injection. For higher doses, higher volumes of aspirin solutions are required. Moreover, solution is acidic; the pH of the solution is about 2.5. Thus, the aspirin solution must be formulated near physiological pH to avoid pain at the injection site and hemolysis. Since aspirin solution is acidic in nature, one way of neutralizing the acidic solution is to treat with an inorganic base. A second approach known in the art is to make basic organic salts of aspirin. Over the past 40 years several scientists have focused on making basic salts of aspirin. The noteworthy or widely popular salt form of aspirin is lysine salt. Extensive research and development activities were carried out on this salt form, but it has been demonstrated to be not as stable as aspirin. Hence, the clinical use of this salt form was restricted to a few hospitals in Germany. Bayer sells this product to a few hospitals with a shelf life of one year. The product they market is a sterile dry powder consisting of 906 mg aspirin lysine salt equivalent to 500 mg of aspirin and 406 mg of l-lysine. In addition, the market presentation included about 50 to 100 mg of glycine as stabilizer. We believe that the product is a sterile dry fill mixture of the lysine salt of aspirin and glycine. This sterile dry mixture is constituted with 5 ml of water for injection to yield a solution containing 100 mg/ml ASA. The 5 ml solution injected in less than 2 minutes. Thromboxane B2 inhibited greater than 95% in 5 minutes of post bolus injection. Inhibition of thromboxane prevents platelet aggregation thus injectable ASA would save life of people suffering from heart attacks.

Our goal was to develop a stable and sterile injectable form of neat aspirin in a vial, which can be reconstituted with s special diluent to yield 100 mg/ml ASA solution. We have conducted extensive research on physical mixtures of aspirin with amino acids and co-lyophilization with amino acids as well as non-aqueous lyophilization. Among the amino acids we tested were arginine, lysine and glycine. We have also tested inorganic basifying agents such as sodium phosphate, dibasic and tribasic, sodium hydroxide, magnesium hydroxide and calcium hydroxide. We have also tested the combinations of amino acids for deprotonation of acetyl salicylic acid with inorganic basifying agents to control the pH of the bulk solution.

In a first aspect of the invention there are provided liquid aspirin-containing compositions having enhanced stability. These compositions are useful as bulk solutions for preparing the lyophilized aspirin. The compositions include aspirin and a cosolvent containing an organic solvent and water. The ratio of the organic solvent to the water being from about 95/5 to 50/50.

The organic solvent is preferably an alcohol such as $C_2$-$C_4$ alcohols. For example, suitable alcohols include t-butyl alcohol (TBA), n-butanol, ethanol and mixtures thereof. In many aspects of the invention, the alcohol is t-butyl alcohol. The ratio of the alcohol to the water can be from about 60:40 to about 80:20. In some aspects, it is preferably from about 65:35 to about 75:25.

The concentration of the aspirin in the composition can be from about 25 mg/ml to about 115 mg/ml. In some aspects, it is preferably from about 45 mg/ml to about 75 mg/ml or about 50 mg/ml.

The liquid aspirin-containing compositions can further include a surfactant, preferably in an amount of from about 0.05 to about 0.5 mg/ml. Suitable surfactants include all pharmaceutically acceptable surfactants known to be useful in lyophilized formulations. In some aspects, the surfactant is polysorbate 80 or Tween 80.

The liquid aspirin-containing compositions can also include a dissolution enhancer, preferably in an amount of from about 2 to about 30 mg/ml, preferably from about 5 to about 20 mg/ml. Suitable dissolution enhancers include without limitation, sucrose or a sugar alcohol, such as mannitol or other pharmaceutically acceptable sugar alcohols known to those of ordinary skill.

The liquid aspirin-containing compositions of the invention can also include a buffer, such as TRIS, i.e. tris (hydroxymethyl)aminomethane, glycine or other amino bases with pKa greater than 8.

The liquid aspiring-containing compositions are suitable for use as a bulk solution in the preparation of lyophilized aspirin. The resultant lyophilized compositions are surprisingly stable with minimal amounts of aspirin degradation to salicylic acid. For example, compositions in accordance with the invention demonstrate after 24 hours at ambient temperature degradation amounts of ≤about 2%, preferably ≤about 1%, ≤about 0.5% or ≤about 0.25%.

One preferred liquid aspirin-containing composition in accordance with the present invention is one in which the cosolvent is a mixture of TBA and water, in a ratio of from about 65:35 to about 75:25. The aspirin is present in an amount of from about 45 to about 75 mg/ml, and composition further includes from about 0.05 to about 0.5 mg/ml polysorbate 80 and from about 5 to about 25 mg/ml mannitol.

In alternative aspects of the invention, the bulk liquid aspirin-containing compositions include cosolvent combinations containing TBA/water, n-butanol/water, ethanol/water, PEG-ethanol/water, DMSO/water, DMF/water or PEG/n-butanol/water.

The invention also includes methods of preparing lyophilized aspirin. The methods include providing the liquid aspirin-containing compositions described, lyophilizing the compositions, and recovering the resultant lyophilized aspirin. The techniques for lyophilizing the aspirin will be apparent to those of ordinary skill and the based upon the disclosure provided in the examples.

The liquid aspirin containing compositions prior to lyophilization can contain from about 20 to about 100 mg/ml of aspirin and the cosolvent includes t-butyl alcohol and water, the ratio of t-butyl alcohol to water being from about 80:20 to about 60:40. In some aspects of the invention, the lyophilized aspirin is crystalline and has a melting point as determined by differential scanning calorimeter or DSC is in the range of 136° C. to 144° C.

The lyophilized aspirin prepared in accordance with the invention can have a shelf life of at least 2 years under ambient storage conditions and will preferably have less than about 2.0% total degradation products after 2 years at 25° C., more preferably, less than about 1.5% or even lower salicylic acid by weight after 2 years at 25° C.

The lyophilized aspirin of the invention will also have low levels of residual t-butyl alcohol therein with amounts of less than about 0.5%, preferably from about 500 to about 10,000 ppm or from about 1,000 to about 3,000 ppm in many aspects.

Another feature of the lyophilized aspirin prepared in accordance with the invention is that when it is lyophilized from a bulk solution having a concentration of about 50, 75 of 100 mg/ml. The lyophilized aspirin can have particle size distributions such as:

| Aspirin conc. | D (0.1) μm | D (0.5) μm | D (0.9) μm | D (1.0) μm |
|---|---|---|---|---|
| 50 mg/ml | 1.8 | 4.5 | 9.1 | 17.6 |
| 75 mg/ml | 1.8 | 4.3 | 8.6 | 15.6 |
| 100 mg/ml | 1.4 | 4.0 | 8.4 | 14.8. |

In an illustrative example of the transformation of the bulk solution to individual containers housing unit dosages of the lyophilized aspirin it is shown that the bulk solution will include a cosolvent wherein the ratio of Cosolvent: TBA/Water (ratio): 55/35 to 75/25
Aspirin: 75 mg/ml to 45 mg/ml
Tween-80: 0.05 to 0.5 mg/ml
Mannitol: 5 mg/ml to 25 mg/ml
Fill volume: 4.66 ml to 7.77 ml.

The vials containing the solution are then lyophilized. Fill volumes are calculated based on 350 mg of Aspirin per vial. It will be reconstituted to 100 mg/ml with 3.5 ml of the diluent which is found in the second containers of the kit, for example. This overage will allow practitioners to withdraw 3.25 ml of solution and thus 325 mg of aspirin from the vial.

The invention also includes a kit for aspirin therapy which contains a first container comprising a therapeutic amount of lyophilized aspirin, for example about 325 mg and a second container comprising water, and a basifying agent for reconstituting the lyophilized aspirin. The second container further comprises a surfactant, preferably in a concentration of from about 0.01 to about 0.4 mg/ml, more preferably about 0.2 mg/ml. The surfactant is polysorbate 80 in many aspects of the invention.

The basifying agent can be selected from suitable amino acids, organic bases and inorganic bases or basic salts of alkaline and alkali metals such as those having a pKa is 8.5 or greater. Some suitable amino acids include arginine, lysine and glycine. An example of a suitable is Tris. Examples of suitable inorganic bases or salt forms include sodium carbonate, sodium bicarbonate and sodium phosphate, dibasic.

The amount of basifying agent included in the second container is an amount sufficient to provide the solution resulting from combining the contents of the first and second containers with a pH of at least about 5.5, preferably about 6.0, more preferably from about 6.0 to about 7.4 or about or near physiological pH.

The invention further includes intravenously-injectable liquid aspirin-containing compositions prepared by combining the contents of the first and second containers in the kit. Such compositions will preferably have a tonicity of from about 270 to about 1300 mOsm/kg.

In accordance with the foregoing one intravenously injectable liquid aspirin containing composition will include from about 20 to about 140 mg/ml, preferably about 100 mg/ml of aspirin, a sugar alcohol, preferably mannitol and a surfactant with less than about 0.1% TBA therein.

The invention also includes methods of providing aspirin therapy. The methods include intravenously administering an effective amount of the liquid intravenously-injectable aspirin-containing compositions described herein to a mammal such as a human in need thereof. In practice, the methods also include combining the contents of the two containers provided preferably in the form of a kit which optionally includes directions for use of the aspirin composition, and intravenously administering the resultant composition. The amount of aspirin administered intravenously can be from about 80 to about 1200 mg, and can preferably be from about 300 to about 1000 mg. In some aspects of the invention, container in which the lyophilized aspirin is placed will contain an amount sufficient to deliver 325 mg of aspirin in a 3.25 ml dose.

The aspirin concentration of the composition intravenously administered can be from about 20 to about 100 mg/ml, or in higher concentrations if desired, and the volume of the intravenously-injectable aspirin-containing composition administered is from about 1 ml to about 10 ml. In some preferred aspects, the concentration of the aspirin administered will be about 100 mg/ml.

The intravenously-injectable aspirin-containing composition can be intravenously administered over a period of about 120 seconds or less and preferably over a period of about 90 seconds or less. Such methods of administration are especially well suited for the treatment of platelet-related thrombosis in the setting of a heart attack or stroke. The compositions of the invention can therefore be advantageously included with ambulances and crash carts used in hospitals and emergency room applications to provide immediate therapeutic action for acute coronary conditions.

Further Methods of Treatment

The reconstituted aspirin compositions described herein can be used in any aspirin therapy know to those of ordinary skill. For example, and without limitation, the aspirin therapy can be used to treat at least one the following:

a) vascular indications including ischemic stroke, TIA, acute MI, prevention of recurrent MI, unstable angina pectoris, chronic stable angina pectoris, b) reducing the combined risk of death and nonfatal stroke or transient ischemia of the brain due to fibrin platelet emboli;

c) reducing the risk of vascular mortality in patients with a suspected acute MI;

d) reducing the combined risk of death and nonfatal MI in patients with a previous MI or unstable angina pectoris, and (4) reduce the combined risk of MI and sudden death in patients with chronic angina pectoris;

e) Revascularization Procedures (Coronary Artery Bypass Graft (CABG), Percutaneous Transluminal Coronary Angioplasty (PTCA), and Carotid Endarterctomy): Aspirin is indicated in patients who have undergone revascularization procedures (i.e., CABG, PTCA or carotid endarterectomy) when there is a preexisting condition for which aspirin is already indicated;

f) Rheumatologic Disease Indications (Rheumatoid Arthritis, Juvenile Rheumatoid Arthritis, Spondyloarthropathies, Osteoarthritis, and the Arthritis and Pleurisy of Systemic Lupus Erythematousus (SLE)): Aspirin is indicated for the relief of symptoms of rheumatoid arthritis, juvenile rheumatoid arthritis, osteoarthritis, spondyloarthropathies, and arthritis and pleurisy associate with SLE. and g) Kawasaki's disease or mucocutaneous lymph node syndrome.

In the case wherein the indication is Kawasaki's disease, the amount of aspirin administered is from about 80 to about 100 mg per kg per day or from about 3 to about 5 mg per kg per day. Other dosage regimens will be apparent to those of ordinary skill without undue experimentation.

EXAMPLES

Example 1

We first evaluated the chemical stability of molar equivalents of physical blends of aspirin with lysine and aspirin with glycine. In the first experiment 5 g of aspirin and 4.06 g of l-lysine were mixed thoroughly in a mortar and pestle and the blend was passed through a 100-mesh screen. A physical blend (906 mg equivalent to 500 mg aspirin) was weighed into several 5 mL, type I, flint glass vials, stoppered and capped. These vials were placed at 40° C. and 25° C. analyzed for aspirin and salicylic acid (major degradant of aspirin) up to three months storage.

Similarly, a physical mixture consisting of 5 g of aspirin and 2.08 g of glycine was prepared and the stability of this physical mixture was similarly evaluated. The stability data are presented in Table 1.

TABLE 1

Solid state stability of physical blends of aspirin with lysine and glycine at 40° C.

| Formulation | Storage time | Aspirin (mg/vial) | % of target | Area % SA |
|---|---|---|---|---|
| Aspirin-Lysine Physical mixture | Initial | 526.4 | 105.3 | 2.20 |
| | 1 M | 482.6 | 96.5 | 2.05 |
| | 2 M | 471.6 | 94.3 | 8.60 |
| | 3 M/25° C. | 495.5 | 94.1 | 5.23 |
| | 1 year/25° C. | 499.9 | 94.9 | 7.52 |
| Aspirin-Glycine Physical mixture | Initial | 485.2 | 97.0 | 0.14 |
| | 1 M | 490.0 | 97.6 | 0.03 |
| | 2 M | 489.4 | 97.9 | 0.14 |
| | 3 M | 501.9 | 102.7 | 0.11 |
| | 1 year/25° C. | 555.6 | 114.5 | 0.53 |

The stability data suggested that aspirin-lysine physical blend is not quite stable as we observed a potency loss of about 6% with a corresponding increase in salicylic acid which is the primary degradant of aspirin. The stability assessment will be based on the formation of salicylic acid during storage. The amount of salicylic acid should not exceed 3% during the shelf life. However, three months' analysis of aspirin-lysine physical blend stored at 25° C. showed formation of about 5% of salicylic acid and about 7.5% at the end of one your storage indicating that the physical blend is not stable.

The physical blend of aspirin-glycine was, however, showed no degradation after a 3-months' storage at 40° C. and one year at 25° C. suggesting that it is feasible to develop a robust formulation of an aspirin-glycine physical blend (1:1 on a molar basis) if one can aseptically blend the sterile aspirin powder with sterile glycine and fill into vials aseptically. This is a labor-intensive and expensive process and may be difficult to source the sterile grade of aspirin as well as glycine. In principle the physical blend can be filled non-aseptically into vials and the finished product can be sterilized by gamma radiation. However, we found in the literature (30) that three degradants were seen by gamma-irradiation of aspirin. Therefore, gamma-irradiation would not be a viable option to sterilize the physical blend of aspirin-glycine.

Example 2

We have also tried to lyophilize aspirin with lysine. Equimolar amounts of aspirin and lysine were dissolved in water to a targeted aspirin concentration in the solution of 50 mg/ml. After stirring for 15 minutes, we observed that part of the ASA was not dissolved. The pH of the solution was 4.5. We added an additional amount of lysine to raise the pH of the bulk solution to 6.5. When all the drug was dissolved, a clear solution was formed. The solution was then filtered and 10 ml aliquots of the solution were placed into 20 cc vials and lyophilized to attain a dose of 500 mg ASA per vial. The product, however, was not lyophilized properly. The lyophilized cake collapsed. HPLC analysis suggested that about 40% of ASA had degraded during the lyophilization process. Based on these data and extensive laboratory studies conducted to produce a stable lyophilized formulation using water and organic bases to dissolve ASA, we have concluded that lyophilization of ASA with lysine or other organic bases using water as dissolution medium is not feasible.

Example 3

In a subsequent set of experiments, we have explored inorganic bases/buffers in water to dissolve ASA, we made a 20 mg/ml slurry of ASA where the solubilization of ASA took place by raising the pH to 6.5 using three different techniques:
3A. Using Sodium hydroxide pellets
3B. Using disodium hydrogen phosphate
3C. Using sodium hydroxide powder to rise pH to 5.0 and then disodium hydrogen phosphate to adjust the pH to 6.5. This procedure allowed us to control pH better than 3A All three solutions were filtered and 5 ml each placed in a Type I flint vials and lyophilized. Upon completion of lyophilization, vials were observed for physical appearance. The lyophilized cakes in all vials were shrunken and collapsed. HPLC analyses suggested that more than 10% of ASA had converted to its major degradant, salicylic acid. Since lyophilization of the ASA-lysine solution was carried out at about −30° C., all water was removed by sublimation at this low temperature. It is not known whether degradation took place during the lyophilization or during the preparation of the bulk solution or combination of both. Therefore, we have investigated the bulk solution stability of example 3C at 25° C. The stability data are presented in the Table-2 below.

TABLE 2

Bulk solution stability of Example 3C at 25° C.

| Assay Time | Amount of Aspirin (mg) | % Initial | Area % of Salicylic Acid |
|---|---|---|---|
| Initial | 98.2 | 100 | 3.1 |
| 4 hours | 90.0 | 90.9 | 9.1 |
| 8 hours | 89.0 | 89.9 | 9.9 |
| 24 hours | 82.5 | 83.3 | 19.1 |

As shown in the above table, about 3% of salicylic acid was initially formed when all ASA dissolved. Salicylic acid levels rose to about 9% within 4 hours. From these experiments, it was clear that aqueous lyophilization of ASA is not feasible. For a robust manufacturing process, we should not observe any degradation of ASA in the bulk solution for lyophilization for at least 24 hours.

Example 4

Since aqueous lyophilization of ASA in the weakly acidic (pH 4-6.5) and weakly basic (above pH 7.0) range is not possible, we have explored the use of non-aqueous solvents to improve the bulk solution stability of ASA. Aspirin is quite soluble in ethanol (80 mg/ml), dimethyl sulfoxide, DMSO, (41 mg/ml) and dimethyl formamide, DMF, (30 mg/ml). Pure ethanol cannot be used for lyophilization as it does not freeze and is very difficult to remove during the lyophilization process without damaging the final finished product. Both DMSO and DMF are caustic solvents which damages polymeric materials such as gaskets and other housing material in the chamber of lyophilizer. Hence these two solvents have been rarely used in the lyophilization process. There are a few products which have used ethanol as a co-solvent with water in the lyophilization process, however, ethanol levels are restricted to 10 to 15% by volume.

Example 5

To overcome the issues around lyophilization with the aforementioned solvents, we have investigated the use of t-butyl alcohol (TBA). TBA is, however, not a powerful aprotic solvent like ethanol, DMSO or DMF. In a first step, we measured the saturation solubility of ASA in pure t-butyl alcohol and binary solvents containing different ratios of water and TBA. It was surprisingly found that aspirin is highly soluble in TBA, much higher (about 1.5 to 4-fold) than the reported solubility of aspirin in ethanol, DMSO and DMF. We also measured the solubility of Aspirin in other C3-C4 aliphatic alcohols such as n-butanol, n-propanol and isopropanol. Also measured solubility of aspirin in other aprotic solvents such as propylene glycol and polyethylene glycol 400. The data summarized in Table-3

The solubility of aspirin even in a TBA/water (60/40) mixture is higher than the solubility of aspirin in pure ethanol. This is really an important invention or finding as incorporation of water in the solvent mixture allows for the presence of water soluble excipients such as bulking agents in the bulk solution for lyophilization. For example, if we want to co-lyophilize ASA with any basic amino acid or with some inorganic basifying agents or bulking agents such as mannitol or sucrose, we need water in the solvent system to dissolve these excipients; as they are not soluble in TBA alone. The solubility data of ASA in different solvents and TBA/water system are presented in Table 3.

TABLE 3

Solubility of ASA in organic solvents and in various ratios of TBA-Water systems

| Solvent system | ~Solubility of Aspirin (mg/ml) |
|---|---|
| Propylene glycol | 155 |
| Polyethylene glycol 400 | 150 |
| n-propanol | 130 |
| isopropanol | 140 |
| n-butanol | 100 |
| TBA | 150 |
| TBA:Water (80:20) | 120 |
| TBA:Water (60:40) | 105 |
| TBA:Water (40:60) | 50 |
| TBA:Water (30:70) | 38 |
| TBA:Water (25:75) | 18 |
| TBA:Water (20:80) | 9 |

As shown in the table above, the solubility of ASA reached its targeted concentration of 100 mg/mL in 80%/20% TBA/water (v/v) system. Please note that all references to a TBA/water ratio in this document is based on (v/v) basis. Generally, the solubility of drugs that are poorly soluble in water, decreases in the mixed solvent systems with increasing water percent. We have observed the same behavior in TBA/water system.

Procedure for Solubility Determination:

A small aliquot of API was added to the vehicle and left on the magnetic stirrer, stirring at 500 RPM and heating if needed until dissolved. Once clear solution was obtained, we added another small portion of drug to facilitate further dissolution of the drug. This process was repeated to obtain the saturation solubility. The solutions were filtered, transferred to vials, stoppered and crimped and used for physical observation and HPLC analysis.

Example 6

As mentioned earlier, the primary criterion for lyophilization is the stability of ASA in the bulk solution. For a robust lyophilization process, the drug should not degrade in the bulk solution for lyophilization for at least 24 hours. We examined the stability of ASA for 24 hours in 80/20, 70/30 and 60/40 TBA/water solutions. No appreciable degradation was observed in all tested systems over a 24-hour storage at ambient storage conditions. The stability data presented in Table 4 below:

TABLE 4

Bulk solution stability of ASA in various compositions of TBA-water system

| Composition of Bulk Solution | ASA concentration | Time Period | Content (mg/mL) | S.A Content |
|---|---|---|---|---|
| TBA:WFI (80:20) | 50 mg/mL | 0 Hrs | 52.0 | 0.11 |
| | | 4 Hrs | 49.6 | 0.13 |
| | | 8 Hrs | 48.7 | 0.14 |
| | | 24 Hrs | 48.4 | 0.34 |
| TBA:WFI (70:30) | 50 mg/mL | 0 Hrs | 46.4 | 0.11 |
| | | 4 Hrs | 53.3 | 0.16 |
| | | 8 Hrs | 51.4 | 0.18 |
| | | 24 Hrs | 52.4 | 0.48 |
| TBA:WFI (60:40) | 50 mg/mL | 0 Hrs | 47.9 | 0.13 |
| | | 4 Hrs | 54.2 | 0.18 |
| | | 8 Hrs | 54.0 | 0.23 |
| | | 24 Hrs | 53.4 | 0.61 |
| TBA:WFI (75:25) | 100 mg/mL | 0 Hrs | 100.3 | 0.26 |
| | | 4 Hrs | 100.3 | 0.39 |
| | | 8 Hrs | 99.9 | 0.53 |
| | | 24 Hrs | 99.5 | 0.64 |
| | | 48 Hrs | 98.7 | 0.64 |
| TBA:WFI (65:35) | 100 mg/mL | 0 Hrs | 101.6 | 0.25 |
| | | 4 Hrs | 100.1 | 0.39 |
| | | 8 Hrs | 100.0 | 0.60 |
| | | 24 Hrs | 99.4 | 0.75 |
| | | 48 Hrs | 99.4 | 0.78 |
| TBA:WFI (60:40) | 100 mg/mL | 0 Hrs | 101.0 | 0.24 |
| | | 4 Hrs | 99.6 | 0.44 |
| | | 8 Hrs | 100.7 | 0.62 |
| | | 24 Hrs | 100.6 | 0.80 |
| | | 48 Hrs | 99.9 | 0.89 |

There are no changes in the physical appearance of bulk solutions during the storage time. Solutions are clear and colorless.

Example 7

Based on the generated information on the solubility and stability of ASA in TBA/water systems, we have undertaken the following lyophilization studies. A 20 mg/ml batch of aspirin in 80% TBA/20 water was prepared where the apparent pH of the bulk solution was 2.9. The pH of the solution was raised to 6.5 using 1N sodium hydroxide. Phase separation was observed, probably due to salting out of inorganic base from TBA/Water system. In the next trial, we first raised the pH of the solution to 5.0 using 1N sodium hydroxide, and then sodium phosphate, dibasic to raise the pH to 6.5. Sodium phosphate, dibasic was used for a better control of pH. Since we still observed phase separation it appears that inorganic bases or buffers may not be compatible with a 80% TBA/20% water system. We may require more water, for example, 70% TBA/30% water in the system to dissolve the alkalinizing agents.

Example 8

Subsequently, we have investigated the possibility of incorporating an organic amino acid base such as arginine, lysine or glycine with ASA in the lyophilization process. Since both lysine and arginine are sparingly soluble in an 80/20 TBA/water mixture we used 70/30 TBA/water as the solvent for lyophilization; the solubility of arginine in this solvent system is about 10 mg/ml, in lysine it is 2 mg/ml, glycine it is 3 mg/ml and in Tris it is 5 mg/ml. Inorganic buffers such as sodium phosphate, dibasic, are not soluble in this solvent system. However, these solubility values are not adequate to neutralize aspirin. Aqueous titration studies have indicated that about 90 mg of arginine is needed to neutralize 100 mg of ASA to make a 20 mg/ml aspirin solution at pH about 6.0. Therefore, among the amino acid buffers arginine and Tris were only amino acid buffer that has reasonable solubility in 70/30 TBA/water system. Hence incorporation of an adequate concentration of amino acid, other than arginine or Tris or inorganic base, to neutralize ASA in TBA/water solvent for co-lyophilization of ASA is not feasible. Even this amount of arginine is not sufficient to completely neutralize ASA. Also, we have measured the solubility of the neat free bases of amino acids in above study without ASA. The solubility of arginine may be different when ASA neutralizes arginine free base in the 70% TBA/30% water system. To test our hypothesis, 2 g of ASA was added to 80 ml of 70/30 TBA/water solvent system. Arginine was slowly added to the clear solution to neutralize aspirin. About 1.8 g arginine was added for complete dissolution. The batch volume was made up to 100 ml with addition of 70/30 TBA/water. Measured arginine solubility is 18 mg/ml which is significantly higher than the solubility of arginine free base alone (~10 mg/ml) The apparent pH of the bulk solution was 6.28.

5 ml aliquots were placed in flint vials and lyophilized. Upon completion of lyophilization, the contents of the vial were reconstituted with 5 ml of Water for Injection. All the drug was dissolved, but a slight haziness was seen. The reconstituted solution pH was 4.71. The bulk solution for lyophilization had 70% TBA, therefore, the pH value of 6.24 was an apparent pH in 70/30 TBA/water system. The reconstituted solution was essentially free of TBA and what was observed was the true intrinsic pH of the 20 mg/ml aspirin solution, which suggest that all ASA was not completely neutralized. A pH of above 6 in the aqueous solution denotes complete neutralization of aspirin.

Example 9

In the next trial, we investigated incorporation of sodium hydroxide to facilitate complete neutralization. To 80 ml of 70/30 TBA/water solvent system and 2 g of aspirin slurry 100 mg sodium hydroxide was added. Arginine was, then, slowly added to the slurry to neutralize aspirin. About 1.6 g arginine was added for complete dissolution. The batch volume was made up to 100 ml with addition of 70/30 TBA/water. The apparent pH of the bulk solution was 6.49. 5 ml aliquots placed in flint vials and lyophilized. Upon completion of lyophilization, the content of vial was reconstituted with 5 ml of Water for Injection. All drug was dissolved, but slight haziness was observed. The reconstituted solution pH was 4.8. Even incorporation free base like sodium hydroxide did not neutralize the aspirin in the 70% TBA/30% water system.

Based on the above studies, it was evident that larger amount of base is needed to neutralize ASA in the preferred solvent system. To incorporate more base in the bulk solution, we explored use of 60/40 TBA/water system as solvent for lyophilization. To 80 ml of 60/40 TBA/water solvent system and 2 g of ASA solution, 400 mg sodium hydroxide was added. The batch volume was made up to 100 ml with addition of 60/40 TBA/water. The apparent pH of the bulk solution was 6.31. 5 ml aliquots were placed in flint vials and lyophilized. Upon completion of the lyophilization, the contents of each vial were reconstituted with 5 ml of Water for Injection. Almost all the drug was dissolved, but a slight haziness was seen. The reconstituted solution pH was 4.41. Even incorporation of a higher amount of a base like sodium hydroxide did not solubilize the aspirin in the bulk solution for lyophilization. The appearance of the lyophilized cake was not good; the cake was shrunken with some melt back. We reconstituted the lyophile with 5 ml of buffer solution containing different concentrations of disodium phosphate. The titration data is presented in Table 5.

TABLE 5

Reconstitution of lyophile with different concentrations of $Na_2HPO_4$

| Concentration of $Na_2HPO_4$ | pH |
|---|---|
| 0 | 4.41 |
| 1 mg/ml | 4.46 |
| 1.25 mg/ml | 4.54 |
| 1.5 mg/ml | 4.62 |
| 1.75 mg/ml | 4.78 |
| 2.0 mg/ml | 4.92 |
| 3.5 mg/ml | 5.21 |

The titration data suggested that the solvent system for lyophilization should hold at least 350 mg of sodium phosphate, dibasic, in addition to 400 mg sodium hydroxide to raise the pH of reconstituted solution to above 5.

Example 10

In all above examples, the reconstituted solutions were hazy. It was not clear whether the haziness was due to low pH or due to the intrinsic nature of the lyophile. We made a batch cited in example 8 and reconstituted to different concentrations using sodium phosphate, dibasic with and without neutral and amphiphilic surfactants. The pH of the reconstituted solution is 4.71. The reconstitution of lyophile to different concentrations in different media are presented in Table 6.

TABLE 6

Physical appearance of Aspirin lyophile at different concentrations in different media

| Reconstituted Medium | Diluents volume | Conc. of drug | Appearance | pH |
|---|---|---|---|---|
| 2.0 mg/mL Disodium hydrogen phosphate | 5.0 mL | 20.0 mg/mL | Slight haziness | 6.49 |
| | 6.7 mL | 15.0 mg/mL | Slight haziness | 6.72 |

TABLE 6-continued

Physical appearance of Aspirin lyophile at different concentrations in different media

| Reconstituted Medium | Diluents volume | Conc. of drug | Appearance | pH |
|---|---|---|---|---|
| anhydrous in WFI | 8.0 mL | 12.5 mg/mL | Slight haziness | 6.84 |
| | 10.0 mL | 10.0 mg/mL | Slight haziness | 7.03 |
| 2 mg/mL of Disodium hydrogen phosphate in 0.05% of Tween80 solution | 5.0 mL | 20.0 mg/mL | Slight haziness | 6.39 |
| | 6.7 mL | 15.0 mg/mL | Slight haziness | 6.70 |
| | 8.0 mL | 12.5 mg/mL | Slight haziness | 6.82 |
| | 10.0 mL | 10.0 mg/mL | Slight haziness | 6.94 |
| 2mg/mL of Disodium hydrogen phosphate and 1 mg/mL TPGS in water for injection | 5.0 mL | 20.0 mg/mL | Slight haziness | 6.33 |
| | 6.7 mL | 15.0 mg/mL | Slight haziness | 6.69 |
| | 8.0 mL | 12.5 mg/mL | Slight haziness | 6.89 |
| | 10.0 mL | 10.0 mg/mL | Slight haziness | 6.96 |

All reconstituted solutions showed haziness at all concentrations despite achieving the target pH. We speculated that the haziness might possible due to degradation of aspirin in the bulk solution. Hence, we tested the lyophile for potency and potential degradation product. HPLC analysis showed a potency loss of 17.4%. Salicylic acid formation was 7.2 area %. There other unknown degradants were observed which are less than 0.2 area %. Possibly the haziness was due to these unknown degradants. Significant potency loss during the lyophilization was a major concern for the development of a robust and stable lyophilized formulation of ASA with a base neutralizer. To confirm whether the instability was found only this batch or other batches, we have analyzed two batches prepared using 70/30 TBA/water as solvent for lyophilization that were stored under ambient conditions over a month. The stability data are presented in Table 7.

TABLE 7

Stability of Aspirin lyophiles stored under ambient conditions for 1 month

| Composition | Potency | % of degradants | | | | |
| | | RRT 0.45 | RRT 0.51 | Salicylic acid | RRT 2.73 | % of Total |
|---|---|---|---|---|---|---|
| Aspirin - 100 mg Arginine - 80 mg NaOH - 2.5 mg | 54.0 | 0.91 | 0.78 | 39.6 | 0.76 | 42.0 |
| Aspirin - 100 mg Arginine - 80 mg NaOH - 3.75 mg | 52.5 | 0.63 | 0.77 | 35.5 | 0.64 | 37.6 |

As shown in the table above, about 50% potency loss was observed in over a month's storage under ambient conditions. Three additional degradation products besides salicylic acid were observed; salicylic acid being the major degradant. Our studies suggested that lyophilization of ASA via partial or complete neutralization using an amino acid or an inorganic base or combination of both in a solvent system containing TBA/water is not feasible. Moreover, the lyophiles obtained in the above examples are amorphous in nature, and ASA is not stable in its amorphous form.

Example 11

Extensive formulation screening studies were conducted to co-lyophilize ASA with different basifying agents, preferably arginine, lysine and Tris, to produce a lyophile that can be upon reconstitution with water result in a clear solution around pH6 or above. These studies have indicated that the bulk solution stability was not adequate to scale up the process. Moreover, the solid state stability of these lyophiles were too poor to produce a commercially viable product. Furthermore, we could not incorporate an adequate amount of water soluble basifying agent in the bulk solution, which was 80% TBA/20% water, for lyophilization to bring the final pH of the reconstituted solution lyophilized product to a value of 6 or above.

The only other approach we have left with is lyophilizing ASA "as is" in (free acid form) TBA/water solvent system without adding any basifying agent. This approach will produce a lyophile of pure ASA which is acidic in nature and not soluble in water upon reconstitution. Therefore, the lyophile would require a special diluent for reconstitution which can neutralize the acidic ASA and produce a clear solution where the final pH of the solution is 6 or greater.

Based on these considerations, we have produced two lyophilized batches by dissolving aspirin to a concentration of 20 mg/ml in 80% TBA/20% water (v/v) solvent system. 5 ml of aliquots were transferred into 10 cc vials and lyophilized. The batch size was 90 ml for the first batch (Example 11A, manufactured on 31 May 2013) and 220 ml for the second batch (Example-11B, manufactured on 3 Sep. 2013). Solid state stability for these two batches were evaluated at different temperatures and the stability data are summarized in the Table 8.

TABLE 8

Solid State Stability of batches-11 A&B

| Batch ID | Storage Temp. | Storage time | % of Initial | Salicylic acid | Area % of total DP* |
|---|---|---|---|---|---|
| Example-11A | | Initial | 100 | 0.69 | 0.79 |
| | 40° C. | 1M | 99.5 | 0.78 | 0.91 |
| | | 2M | 99.7 | 1.72 | 1.82 |
| | | 3M | 99.4 | 0.92 | 0.99 |
| | | 6M | 99.3 | 0.68 | 0.73 |
| Example-11B | | Initial | 100.0 | 0.10 | 0.10 |
| | 40° C. | 1M | 99.4 | 0.32 | 0.37 |
| | | 2M | 100.1 | 0.48 | 0.53 |
| | | 3M | 95.0 | 0.55 | 0.60 |
| | | 6M | 101.6 | 0.89 | 1.00 |
| | 30° C. | 3M | 99.8 | 0.39 | 0.43 |
| | | 6M | 97.1 | 0.46 | 0.50 |
| | | 9M | 96.0 | 0.68 | 0.71 |
| | | 12M | 96.3 | 0.66 | 0.72 |
| | 25° C. | 3M | 99.7 | 0.31 | 0.35 |
| | | 6M | 99.4 | 0.36 | 0.40 |
| | | 9M | 99.0 | 0.50 | 0.53 |
| | | 12M | 99.6 | 0.55 | 0.58 |
| | | 18M | 98.8 | 0.67 | 0.72 |

*DP: Degradation products, sum of known and unknown degradants

As shown in the table above, we have produced extremely stable product as insignificant potency loss was observed at 40° C., over a 6-month storage. It is unusual for a lyophilized product to show no potency loss under this accelerated condition.

Since the lyophilization of neat ASA produced a stable lyophile, we have optimized the lyophilization cycle and the final lyophilization conditions are presented in Table 9.

TABLE 9

General lyophilization conditions followed to lyophilize ASA in TBA/Water system

| Steps | Condition | Shelf Temp, ° C. | Time, Min | Pressure, m Torr |
|---|---|---|---|---|
| Loading | | RT | — | — |
| Freezing | | | | |
| | | −40° C. | 4-8 hours | — |
| Primary | | −40° C. to −10° C. | | 200 |
| Drying | | | | 200 |
| | | −10° C. to 0° C. | | 200 |
| | | 0° C. | 240 18-22 hours | 200 |
| | | 0° C. to 25° C. | 180 | 150 |
| Secondary drying | | 25° C. | 840 10-12 hours | 150 |
| N$_2$ Back fill | — | 25° C. | — | ~11 Psia |
| Stopper the vials, seal them with aluminum caps | | | | |

Example 12

After optimization of lyophilization cycle, two lyophilized batches were manufacture by dissolving aspirin to a concentration of 20 mg/ml in 80% TBA/20% water (v/v) solvent system. Aliquots of 5 mL were transferred into 10 cc vials and lyophilized. The batch size was 1,000 ml for the first batch (Example 12A) and 900 ml for the second batch (Example-12B). Solid state stability of these two batches were evaluated at different temperatures and the stability data are summarized in Table 10. We have conducted stability studies up to 6 months at 40° C., and 9 months at 30° C. and 25° C. for the batch-12A. For the batch-12B, we have conducted stability studies up to 6 months at 40° C., and up to 12 months at 30° C. and up to two years at 25° C. Both batches exhibited outstanding stability; only 1.4% potency loss was seen after 24 months' storage at 25° C. while the salicylic acid content increased from 0.1% to 0.48% for the batch-12B. There are no other degradant peaks observed that were above the limit of quantification of the method. We have not observed any degradation even under accelerated conditions and no shrinkage of cake even after storing at 40° C./6M. This was quite unusual and unexpected for a lyophilized product to exhibit extraordinary stability at 40° C./6M storage condition. The data clearly demonstrated that the lyophilization process where ASA present predominantly in the unionized form surprisingly and unexpectedly produced a very stable ASA product. The stability data are presented in the Table 10.

TABLE 10

Solid State Stability of ASA batches-12 A&B

| Batch ID | Storage/Time | | Mg/vial | % of Initial | Salicylic Acid |
|---|---|---|---|---|---|
| Example 12A | Initial | | 99.4 | 100.0 | 0.09 |
| | 40° C. | 2M | 96.1 | 96.7 | 0.56 |
| | 75% | 3M | 94.4 | 95.0 | 0.66 |
| | RH | 6M | 99.4 | 100.0 | 0.41 |
| | 30° C. | 3M | 95.4 | 96.0 | 0.43 |
| | 65% | 6M | 101.9 | 102.5 | 0.55 |
| | RH | 9M | 102.3 | 102.9 | 0.59 |
| | 25° C. | 3M | 100.8 | 101.4 | 0.29 |
| | 60% | 6M | 96.4 | 97.0 | 0.77 |
| | RH | 9M | 101.0 | 101.6 | 0.45 |
| Example 12B | Initial | | 100.1 | 100.0 | 0.10 |
| | 40° C. | 1M | 99.3 | 99.2 | 0.21 |
| | 75% | 3M | 102.2 | 102.1 | 0.22 |
| | RH | 6M | 97.0 | 96.9 | 0.29 |
| | 30° C. | 3M | 99.4 | 99.3 | 0.13 |
| | 65% | 6M | 98.5 | 98.4 | 0.24 |
| | RH | 9M | 97.1 | 97.0 | 0.26 |
| | | 12M | 97.4 | 97.3 | 0.46 |
| | 25° C. | 3M | 99.1 | 99.0 | 0.11 |
| | 60% | 6M | 102.6 | 102.5 | 0.16 |
| | RH | 9M | 100.7 | 100.6 | 0.22 |
| | | 12M | 98.7 | 98.6 | 0.31 |
| | | 18M | 99.9 | 99.8 | 0.37 |
| | | 24M | 98.7 | 98.6 | 0.48 |
| | | 39M | 97.9 | 97.8 | 0.59 |

Example 13

One aspect of this invention was to produce a stable lyophilized product and a solvent system with sufficient bulk solution stability to withstand an aseptic processing and lyophilization process. The lyophilized products we have manufactured in most of these studies were made with 80% TBA/20% to 60% TBA/40% water solvent system and the bulk solution for lyophilization stable for 24 hours with minimal degradation. We have achieved this goal. The second aspect of the invention is to identify an appropriate diluent to reconstitute the lyophile to a concentration of ASA about 20 mg/ml to about 100 mg/ml. The criteria for the diluent is that the neutralizing agent is acceptable and widely used in the injectable formulations, and the pH of the reconstituted solution should be between pH 5.5 to 7.4 (closer to physiological pH) at the target concentration of 20 to 100 mg ASA/ml. Using these boundary conditions, we have screened various organic and inorganic basifying agents in the diluent to reconstitute the ASA lyophile. The reconstitution studies were done by reconstituting a 100 mg vial with 5 ml of solution containing a buffer or a basifying agent or a combination of both. All tested basifying agents are presented in the Table 11.

TABLE 11

Reconstitution of ASA lyophile with various basifying agents

| Basifying agent | Amount added (mg) | Final pH |
|---|---|---|
| Arginine | 127.5 | 6.2 |
| Arginine | 90 | 6.2 |
| Sodium carbonate | 38.1 | 6.2 |

TABLE 11-continued

Reconstitution of ASA lyophile with various basifying agents

| Basifying agent | Amount added (mg) | Final pH |
|---|---|---|
| Sodium bicarbonate | 58.65 | 8.2 |
| Sodium bicarbonate | 50.0 | 6.5 |
| Arginine/NaOH | 80.0/5.0 | 7.0 |
| NaOH | 20 | 6.2 |
| Arginine/NaOH | 80.0/4.0 | 6.5 |
| Arginine/NaOH | 80.0/3.0 | 6.4 |
| Arginine/NaOH | 40.0/10.0[1] | 6.1 |
| Arginine/NaOH | 80.0/4.0[1] | 6.8 |
| Magnesium Oxide | 5.4 | 6.0 |
| Magnesium Oxide | 3 | 5.8 |
| Calcium hydroxide | 5.14 | undissolved |
| Manganese oxide | 6.03 | 5.0 |
| Tris | 80 | 6.4 |
| Lysine | 93.0 | 6.0 |
| Sodium phosphate, dibasic | 100.0 | 6.25 |

[1]Reconstitution concentration is 40 mg/ml

The basifying agents are not limited to what we have tested. Basic oxides, hydroxides and salts of any inorganic alkaline and alkali metals can be used. Similarly, organic bases with pKa above 8.5 can be used to reconstitute the aspirin lyophile. The quantity of basifying agent required to dissolve all aspirin, and to bring the pH of the solution about 6.0 can be determined by titrating 20 mg/ml to 100 mg/ml aspirin slurry with a basifying agent.

Example 14

The solubility of ASA is greater than 100 mg/ml at pH 5.5 and above. In the next phase of invention, we have determined the amount of base required to obtain different concentrations of ASA solutions. We have conducted the study using different concentrations of sodium phosphate, dibasic, to obtain different concentrations of aspirin up to 100 mg/ml. Data are presented in Table 12.

TABLE 12

Titrations of various basifying agents to obtain different concentration of ASA

| Diluent/Conc. (mg/ml) | Recon. volume(ml) | Aspirin Conc. (mg/ml) | pH |
|---|---|---|---|
| $Na_2HPO_4$/20 | 5 | 20 | 6.25 |
| $Na_2HPO_4$/25 | 4 | 25 | 6.21 |
| $Na_2HPO_4$/33.3 | 3 | 33.3 | 6.18 |
| $Na_2HPO_4$/50 | 2 | 50 | 6.25 |
| Tris/16.0 | 5 | 20 | 5.8 |
| Tris/17.4 | 4 | 25 | 6.23 |
| Tris/34.8 | 2 | 50 | 6.41 |
| Tris/69.6 | 1 | 100 | 5.86 |

It should be noted that the concentration of basifying agent to neutralize ASA solution proportionately increases with increase in the concentration of ASA. Titration data for other amino acids can be obtained similarly.

Example 15

All the reconstituted solutions presented in examples 13 and 14 have shown slight haziness. The presence of haziness is concentration independent. However, when the ASA API constituted under identical conditions, the resulting solution did not show any haziness. Several studies were conducted without any success to identify the origin of the haziness. When the reconstituted solution was filtered through a 0.2μ filter, the haziness disappeared. However, there was no change in the concentration of ASA before and after filtration suggesting that the haziness was intrinsically present in the lyophile. When we reconstituted with a basifying agent containing 0.01% or 0.05% polysorbate 80, the haziness disappeared. The haziness is probably due to the presence of residual TBA in the lyophile. The diluent or the solution for reconstitution will, therefore, contain 0.01% to 0.05% polysorbate 80.

Since the aspirin product will be administered via an IV bolus route, tonicity of the final reconstituted solution is a critical factor to avoid pain at the injection site. Hence, we reconstituted the lyophile containing 500 mg per vial with selected diluents to different concentrations and measured their tonicity. The data are presented in Table 13.

TABLE 13

Tonicity values of reconstituted solutions of ASA at different concentrations

| Nature of buffer | Reconstitution Volume | ASA Concentration | Osmolality (m.Osm/Kg) | pH |
|---|---|---|---|---|
| 20 mg/mL Na$_2$HPO$_4$ with 0.05% Tween80 | 25 mL | 20 mg/mL | 481 | 6.09 |
| 50 mg/mL Na$_2$HPO$_4$ with 0.05% Tween80 | 10 mL | 50 mg/mL | 1172 | 6.17 |
| 34 mg/mL Tris Buffer | 10 mL | 50 mg/mL | 540 | 5.79 |
| 34 mg/mL Tris Buffer with 0.05% Tween80 | 10 mL | 50 mg/mL | 549 | 5.84 |
| 17.5 mg/mL Tris Buffer with 0.05% Tween80 | 20 mL | 25 mg/mL | 269 | 5.97 |
| 40 mg/mL L-Lysine | 20 mL | 25 mg/mL | 380 | 7.97 |
| 40 mg/mL of L-Lysine with 0.05% Tween80 | 20 mL | 25 mg/mL | 388 | 8.10 |
| 12 mg/mL Na$_2$HPO$_4$ and 27 mg/mL of Tris buffer with 0.05% Tween80 | 10 mL | 50 mg/mL | 717 | 6.14 |

TABLE 13-continued

Tonicity values of reconstituted solutions of ASA at different concentrations

| Nature of buffer | Reconstitution Volume | ASA Concentration | Osmolality (m.Osm/Kg) | pH |
|---|---|---|---|---|
| 30 mg/mL of lysine and 7.5 mg/mL of Tris buffer | 20 mL | 25 mg/mL | 338 | 7.53 |
| 68 mg/mL Tris Buffer with 0.05% Tween80 | 10 mL | 100 mg/mL | 1060 | 6.07 |
| 68 mg/mL Tris Buffer with 0.05% Tween80 Aspirin API 1 g | 10 mL | 100 mg/mL | 1036 | 5.89 |

As shown in the table, the osmolality values are higher for 50 mg/ml ASA solutions compared to the 25 mg/ml solutions. Phosphate buffer may not be an ideal basifying agent due to the high tonicity of the reconstituted solutions. Based on these data, tris or lysine or combination of tris and lysine could be the ideal basifying agents that can be included in the diluent to reconstitute ASA lyophile.

We have conducted IV irritation studies by injecting ASA solution of different osmolalities (300 to 1300 mOsm/kg) in rabbit ear vein. Surprisingly, no irritation was observed even with solutions of high osmolality of 1300. It is an unexpected discovery or finding.

Example 16

The next step of development is to ensure that the selected buffer system not only produces a clear colorless solution but also has adequate solution stability. We have taken 1 g strength lyophilized vials and reconstituted the vial with the proper volume of the buffer solution to produce 25, 50 and 100 mg/ml ASA concentration. We have measured the pH and tonicity values of the final reconstituted solutions. Solution stability studies were carried out over a period of 8 hours. The data are presented in Table 14.

TABLE 14

Reconstitution stability of Aspirin (25, 50 & 100 mg/ml) in selected buffer in system

| Batch ID | Buffer Diluent conc. | Recon. volume | Aspirin conc. | Time | Conc. (mg/ml) | % of Initial | Osmolality m.Osm/kg | pH |
|---|---|---|---|---|---|---|---|---|
| 16A | 17.5 mg/mL Tris with 0.05% PS80 | 40 mL | 25 mg/mL | Initial | 24.6 | 100.0 | 271 | 6.86 |
|  |  |  |  | 2 hrs | 24.1 | 98.1 |  |  |
|  |  |  |  | 4 hrs | 24.0 | 97.5 |  |  |
|  |  |  |  | 8 hrs | 23.1 | 93.6 |  |  |
| 16B | 17.5 mg/mL Tris and 2 mg/ml Na$_2$HPO$_4$ with 0.05% PS80 | 40 mL | 25 mg/mL | Initial | 24.2 | 100.0 | 300 | 7.10 |
|  |  |  |  | 2 hrs | 23.5 | 97.4 |  |  |
|  |  |  |  | 4 hrs | 23.0 | 95.4 |  |  |
|  |  |  |  | 8 hrs | 22.4 | 94.1 |  |  |
| 16C | 34 mg/mL of Tris and 2 mg/mL Na$_2$HPO$_4$ with 0.05% PS80 | 20 mL | 50 mg/mL | Initial | 45.2 | 100.0 | 571 | 6.66 |
|  |  |  |  | 2 hrs | 43.7 | 96.7 |  |  |
|  |  |  |  | 4 hrs | 43.6 | 94.4 |  |  |
|  |  |  |  | 8 hrs | 42.0 | 92.9 |  |  |
| 16D | 50 mg/mL Na$_2$HPO$_4$ with 0.05% PS80 | 20 mL | 50 mg/mL | Initial | 44.8 | 100.0 | 1170 | 5.95 |
|  |  |  |  | 2 hrs | 43.5 | 96.9 |  |  |
|  |  |  |  | 4 hrs | 43.3 | 96.7 |  |  |
|  |  |  |  | 8 hrs | 42.2 | 94.0 |  |  |
| 16E | 68 mg/mL of Tris with 0.05% PS80 | 10 mL | 100 mg/mL | Initial | 106.9 | 100.0 | 1060 | 5.92 |
|  |  |  |  | 4 hrs | 99.6 | 93.2 |  |  |
| 16F | 68 mg/mL of Tris Buffer | 10 mL | 100 mg/mL | Initial | 109.3 | 100.0 | 1038 | 5.83 |

As shown in the table, the tonicity values were higher for higher concentrations of ASA solutions. About 6% potency loss occurred over an 8-hour period for solutions reconstituted to 25 and 50 mg/ml concentration. All reconstituted solutions with exception of 16F are clear at the end of 8 hours' storage time. In the case of 16F, the vial was reconstituted with buffer only without polysorbate 80. The solution was hazy and remined hazy at the end of 8 hours.

Example 17

In example 12, we have presented stability data of two batches of lyophile. The unusual stability of these two batches and two other earlier exploratory batches could be due to the formation of a solvate of ASA with TBA or due to the formation of crystalline ASA lyophilizate. All lyophiles have residual TBA in the range of 1000-3000 ppm. Differential scanning calorimetry (Perkin-Elmer, Model # DSC 4000) analysis of these sample showed a distinct melting endotherm suggesting that the drug may present in the crystalline form. We have conducted lyophilization studies ASA bulk solution at different concentrations of aspirin, i.e., 25 mg/ml. 50 mg/ml and 100 mg/ml to determine if the concentration of aspirin in the bulk solution would have effect on the stability. All these batches showed excellent chemical stability. No loss in potency was seen in all these batches over a 6-month storage at 40° C. These data suggest that the stability of ASA lyophile is independent of aspirin concentration in the bulk solution. Thermal analysis data presented in Table 15.

TABLE 15

Thermal data of various batches of ASA lyophile

| ID | Solvent system | Aspirin conc. | Onset | Melting Pt | Enthalpy $\Delta_{fus}H(J/g)$ |
|---|---|---|---|---|---|
| R11-API | Plain API | — | 136.29° C. | 140.19° C. | 126.1 |
| R11-52 | 80% TBA:20% WFI | 50 mg/mL | 132.00° C. | 136.24° C. | 139.0 |
| R11-53 | 80% TBA:20% WFI | 50 mg/mL | 132.63° C. | 136.83° C. | 111.0 |
| R11-56 | 80% TBA:20% WFI | 50 mg/mL | 128.55° C. | 133.31° C. | 136.0 |
| R11-57 | 80% TBA:20% WFI | 75 mg/mL | 134.04° C. | 136.70° C. | 161.5 |
| R11-58 | 80% TBA:20% WFI | 100 mg/mL | 132.13° C. | 135.95° C. | 211.1 |
| R11-59 | 15% Ethanol:85% WFI | 6 mg/mL | 125.54° C. | 129.59° C. | 166.0 |
| R11-60 | 80% Ethanol:20% WFI | 50 mg/mL | 126.47° C. | 132.35° C. | 160.0 |

As shown in the table, melting points and enthalpies of fusion ($\Delta_{fus}H$) of the lyophilized aspirin made with different concentrations, using either TBA/water or ethanol/water, are different from the API—melting points of lyophile are lower and enthalpies are higher. Enthalpy of the lyophile was increasing with increasing in the concentration of ASA in the bulk solution. Higher enthalpy coupled with lower melting point for the lyophilized ASA suggest that a new crystal form or the crystalline material as API of ASA may have formed during the lyophilization. Further investigation to understand the crystalline nature or crystal habit of the lyophilized aspirin product was carried out.

Additionally, we have measured the particle size distribution of the lyophiles and API. The measurement of particle size (Malvern, Master sizer 2000) of all the samples were done by using dry powder volume distribution method. The data are presented in Table 16. As shown in the table, the particle size distribution of lyophilized products, made with different concentrations of aspirin in the TBA/water solvent system, is significantly smaller compared to the API used to make these batches. For example, the average particle size of 10% of particle is about 11.4 μm for API while the particle size diameter of lyophilized product made with 100 mg/ml aspirin concentration was 1.4 μm—a 10-fold decrease in the particle diameter. Similar trends were seen for D50%, D90% and D100%. Also, particle size of lyophile decreases with increasing the concentration of aspirin in the bulk solution.

TABLE 16

Particle size distribution of Aspirin API & lyophile

| Aspirin conc. | D10% (μm) | D50% (μm) | D90% (μm) | D100% (μm) |
|---|---|---|---|---|
| API | 11.4 | 92.9 | 249.5 | 431.0 |
| 50 mg/ml | 1.8 | 4.5 | 9.1 | 17.6 |
| 75 mg/ml | 1.8 | 4.3 | 8.6 | 15.6 |
| 100 mg/ml | 1.4 | 4.0 | 8.4 | 14.8 |

Example 18

Since the thermal data of the lyophilized product were significantly different the API that was used to produce the lyophiles and the presence of a distinct melting endotherm suggest that the lyophilization of ASA in TBA/water solvent system might have produced a crystalline material in the vial. We have submitted lyophilized samples made with 50 and 100 mg/ml aspirin concentration in TBA/water and 50 mg/ml aspirin concentration in ethanol/water system for X-ray analysis. X-ray (Burker AXS) diffractograms of these samples are presented in FIGS. 1a-1d. As shown in the figures, the X-ray diffractograms clearly demonstrated that the lyophilization of ASA in TBA/Water solvent system produced a crystalline material which is similar to the crystalline nature of the API. Salient points are noted below.

1. A split peak was seen at 2θ=26.7-26.9 in the samples lyophilized using TBA/water solvent system only. It was absent in the API and the lyophiles made in ethanol/water system.
2. Intensity of all peaks in the lyophiles made in TBA/water system are significantly higher than the corresponding peaks in the API.
3. Intensity of peaks increases with increase in the concentration of aspirin in the bulk solutions of TBA/water solvent system.
4. The height of the largest peak for API and lyophile made with 50 mg/ml aspirin concentration was about 30,000 counts, while it was over 60,000 counts for the lyophile made with 100 mg/ml aspirin concentration in the bulk solution.
5. Lyophiles made with ethanol/water, we have noted that the peak at 2θ=7.7 was the largest peak and the peak at 2θ=15.6 was the second largest while the largest peak for the API and all lyophilized batches made in TBA/water system is at 2θ=15.6

6. The largest peak for the lyophile made with ethanol is about 160,000 counts which is significantly higher compared to API and other. The summary of X-ray analysis is presented in the table below.

TABLE

Summary of ratio of major peaks of X-ray diffractogram of lyophiles

| Batch ID | Bulk solution concentration | TGA -% LOD | XRD Intensities at 2θ | | |
|---|---|---|---|---|---|
| | | | 7.7 | 15.6 | 26.7-26.9 |
| | API-Crystalline | — | 37.9 | 100 | 4.9 |
| R11-52 | TBA:WFI (80:20)-50 mg/ml | — | 69.6 | 100 | 72.3* |
| R11-57 | TBA:WFI (80:20)-75 mg/mL | 0.40 | 50.8 | 100 | 60.3* |
| R11-58 | RTBA:WFI (80:20)-100 mg/mL | 0.45 | 62.7 | 100 | 66.3* |
| R11-59 | Ethanol:WFI (15:85)-16.7 mg/mL | 0.17 | 100 | 54.0 | 13.8 |
| R11-60 | Ethanol:WFI (80:20)-50 mg/ml | 0.10 | 100 | 44.4 | 11.3 |

*Sum of doublet at 26.8 & 26.9

Loss on drying about 0.4% by TGA suggested the presence of residual TBA in the lyophile. Based on Thermal and X-ray analysis, we believe that the crystalline material obtained through lyophilization either with TBA/water or with ethanol/water is different from the crystal habits of API.

Example 19

In example 17, we have evaluated the lyophiles that were prepared at different concentrations of ASA in 80% TBA/20% water. X-ray analyses data suggested that the crystalline material was consistently produced during the lyophilization process regardless of ASA concertation in the bulk solution for lyophilization. X-ray diffractograms pattern of all these lyophiles are similar. Next part of our invention, we have evaluated the effect of varying concentrations of TBA in the bulk solution for lyophilization at a constant ASA concertation of 100 mg/ml during the lyophilization process. We tested the lyophiles made from with neat TBA to 70:30 TBA:Water systems (Examples-19A to 19E below). All the lyophiles are crystalline in nature. The X-ray diffractogram patterns were consistent with what we have observed in the earlier examples. These data suggest that the lyophilization process is rugged and consistently produce the same crystalline form of ASA regardless of concentrations of ASA or TBA in the solvent system used for lyophilization. Our invention not only produced crystalline form during the conventional lyophilization process but also the crystalline lyophilizate thus formed is independent of either ASA concertation or the concertation of TBA in the solvent system used for lyophilization. These findings are quite unique, and to the best of our knowledge it was never observed for any other molecules using TBA as solvent for lyophilization.

Solid state stability of these lyophiles were evaluated and the stability data are presented in the Table 16. As shown in the table all lyophiles showed excellent stability as previously observed with the earlier batches.

These lyophiles when reconstituted with the special diluent to 100 mg/ml ASA concentration, dissolves slowly. The reconstitution time varies 3 to 5 minutes. During the reconstitution, we did observe that vigorous shaking was required to break the lyophilizate. This was attributed to the wettability of the cake. Hence, we prepared a lyophile (Example-19F) containing 10 mg/ml mannitol to improve the porosity of the lyophilizate. Since the aqueous solubility of mannitol is quite high, the mannitol dissolves first during the reconstitution thereby providing channels for the diluent to wet and dissolve ASA. As expected, we did improve the reconstitution time from 3 to 5 minutes to about 3 minutes. Presence of mannitol did not adversely affect the stability of ASA.

TABLE 16

Stability of ASA lyophiles produced with varying concentrations of TBA

| Example | Bulk solution Composition | ASA concentration in bulk solutiom | Storage and time period | | Content (mg/vial) | Salicylic Acid | % Moisture | TBA Content (ppm) |
|---|---|---|---|---|---|---|---|---|
| -19A | Neat TBA | 100 mg/ml | 40° C./75% RH | 1M | 480.9 | 0.36 | ND | 4166 |
| | | | | 2M | 520.5 | 0.52 | ND | ND |
| | | | Initial | | 501.1 | 0.30 | ND | 5640 |
| | | | 40° C./75% RH | 2M | 526.1 | 0.56 | ND | ND |
| -19B | TBA:WFI (90:10) | 100 mg/ml | Initial | | 473.1 | 0.36 | 0.03 | 7320 |
| | | | 40° C./75% RH | 1M | 481.5 | 0.16 | 0.05 | 6433 |
| | | | | 3M | 481.3 | 0.18 | 0.07 | 9401 |
| | | | | 6M | 491.9 | 0.23 | 0.09 | ND |
| -19C | TBA:WFI (75:25) | 100 mg/ml | Initial | | 552.7 | 0.64 | 0.18 | 6947 |
| | | | 40° C./75% RH | 1M | 506.2 | 0.26 | ND | 4902 |
| | TBA:WFI (75:25) | 100 mg/ml | Initial | | 476.3 | 0.31 | ND | 3809 |
| | | | 40° C./75% RH | 2M | 528.2 | 0.56 | ND | ND |
| -19D | TBA:WFI (70:30) | 100 mg/ml | Initial | | 480.6 | 0.40 | 0.08 | 1607 |
| | | | 40° C./75% RH | 1M | 502.7 | 0.17 | 0.08 | 1558 |
| | | | | 3M | 501.2 | 0.18 | 0.10 | 1107 |
| | | | | 6M | 507.2 | 0.17 | 0.11 | ND |

TABLE 16-continued

Stability of ASA lyophiles produced with varying concentrations of TBA

| Example | Bulk solution Composition | ASA concentration in bulk solutiom | Storage and time period | | Content (mg/vial) | Salicylic Acid | % Moisture | TBA Content (ppm) |
|---|---|---|---|---|---|---|---|---|
| -19E | TBA:WFF (70:30) | 100 mg/ml | Initial | | 519.4 | 0.23 | 0.22 | 968 |
| | | | 40° C./75% RH | 1M | 448.4 | 0.25 | ND | ND |
| | | | | 2M | 483.4 | 0.25 | 0.25 | ND |
| | | | | 3M | 528.7 | 0.41 | 0.23 | ND |
| | | | 25° C./60% RH | 3M | 497.4 | 0.54 | 0.22 | ND |
| -19F | Mannitol- 10 mg/ml TBA:WFI (70:30) | 100 mg/ml | Initial | | 535.7 | 0.26 | 0.17 | 217 |
| | | | 40° C./75% RH | 1M | 497.7 | 0.28 | ND | ND |
| | | | | 2M | 497.7 | 0.28 | ND | ND |
| | | | | 3M | 528.7 | 0.47 | ND | ND |
| | | | 25° C./60% RH | 3M | 540.7 | 0.65 | ND | ND |

Example 20

One aspect of our discovery was to produce a robust lyophilization process where we can consistently produce crystalline ASA during the lyophilization regardless of concentrations of critical components such as TBA, water and ASA. This aspect of invention had been successfully accomplished. Second critical aspect of inventions is produce a lyophile with less than a minute reconstitution time, when reconstituted with a special diluent to 100 mg/ml ASA concentration. Rapid dissolution is very critical to our invention as the intent of this dosage form is to treat patients with Acute Coronary Syndrome (ACS) who require urgent medical intervention. As mentioned earlier, the lyophilizate produced using 80:20 TBA:Water as bulk solution for lyophilization produced a dense cake. When reconstituted with the special diluent, the cake does not get wet and requires vigorous shaking. The lyophilizate dissolves completely after five minutes of vigorous shaking.

To develop a rapid dissolution lyophilizate, one need to improve the porosity and wettability of the cake. Porosity of the cake can be improved by reducing solid contents per mL of bulk solution for lyophilization. For example, the porosity of the lyophilizate increases if we decrease the solid contents. Therefore, we decreased ASA concentration to 50 mg/ml from 100 mg/ml in the bulk solution for lyophilization. Incorporation of small amount of surfactant such as polysorbate 80 would improve the wettability of the cake. To determine the effect of a lower concentration ASA and the presence of small amount of surfactant, we prepared bulk solutions containing 80:20 TBA:WFI with 50 mg/ml ASA concertation and different levels of polysorbate 80 (-20A to -20D). When reconstituted these lyophiles with the special diluent, we observed that reconstitution times were about 5 minutes for -20A,B&C and the reconstituted solutions are slightly hazy. The reconstituted time for -20D is, however, improved to 3 minutes and the solution is clear. The solid-state stability date of these lyophiles are presented in Table 17. As shown in the table, presence of polysorbate 80 has no effect on the stability of ASA.

TABLE 17

Stability of ASA lyophiles produced with varying concentration of PS-80

| # | Bulk solution Composition | ASA concentration in bulk solution | Storage Temp./Time | | Content (mg/vial) | % Salicylic Acid | % of Moisture | TBA Content (ppm) |
|---|---|---|---|---|---|---|---|---|
| 20A | TBA:WFI (80:20) | 50 mg/ml | Initial | | 477.4 | 0.20 | 0.36 | 12534 |
| 20B | Tween80- 0.1 mg/ml TBA:WFI (80:20) | 50 mg/ml | Initial | | 485.7 | 0.34 | ND | ND |
| | | | 40° C./75% RH | 1M | 526.1 | 0.72 | ND | ND |
| 20-C | Tween 80 0.5 mg/ml TBA:WFI (80:20) | 50 mg/ml | Initial | | 570.6 | 0.56 | 0.14 | 2898 |
| | | | 40° C./75% RH | 1M | 544.9 | 0.51 | 0.12 | 3891 |
| | | | | 3M | 578.2 | 0.61 | 0.10 | 2459 |
| 20D | Tween 80- 1.0 mg/ml TBA:WFI (80:20) | 50 mg/ml | Initial | | 505.5 | 0.53 | 0.31 | 7149 |
| | | | 40° C./75% RH | 1M | 516.6 | 1.11 | 0.28 | 4281 |
| | | | | 3M | 482.9 | 0.89 | 0.30 | 4019 |
| | | | 40° C./75% RH | 1M | 448.4 | 0.25 | ND | ND |
| | | | | 2M | 483.4 | 0.25 | 0.25 | ND |
| | | | | 3M | 528.7 | 0.41 | 0.23 | ND |
| | | | 25° C./60% RH | 3M | 497.4 | 0.54 | 0.22 | ND |

Example 21

Another aspect of invention is to produce the lyophile with low levels of residual TBA and a reconstitution time of less one minute. In example 19 (-19B to -19D), we have observed that the increase in percent of water in the bulk solution for lyophilization decreases the residual TBA content in the lyophile. In example 20 (20A-20D), decrease in concentration of ASA in the bulk solution and incorporation of small amount of polysorbate 80 would reduce the reconstitution time. To further fine tune the lyophilizate formulation, we employed 65:35 TBA:Water as bulk solution for lyophilization, ASA at 50 mg/ml, polysorbate 80 at 0.1 mg/ml to enhance wettability of cake, in the presence of different bulking agents such as sucrose, lactose and mannitol. In all three cases we obtained lyophiles with a porous cake and the reconstitution time was instantaneous—as we are adding the special diluent, the contents of the vial were instantaneously going into solution. We have conducted limited stability on these formulations, and the stability is comparable to earlier batches.

TABLE 18

Stability of ASA lyophiles produced with different bulking agents

| Bulk solution Composition | ASA concentration in bulk solution | Storage Temp./ Time | Content (mg/vial) | % Salicylic Acid | % of Moisture | TBA Content (ppm) |
|---|---|---|---|---|---|---|
| Mannitol-10 mg/ml Tween80-0.1 mg/ml TBA:WFI (65:35) | 50 mg/ml | Initial 40° C./75% RH 1M | 493.8 546.4 | 0.40 0.67 | ND ND | 8034 ND |
| Sucrose-10 mg/ml Tween80-0.1 mg/ml TBA:WFI (65:35) | 50 mg/ml | Initial 40° C./75% RH 1M | 479.1 545.2 | 0.37 0.61 | ND ND | 8308 ND |
| Lactose monohydrate - 10 mg/ml 50 mg/ml Tween80- 0.1 mg/ml TBA:WFI (65:35) | 50 mg/ml | Initial 40° C./75% RH 1M | 483.9 511.9 | 0.37 0.68 | ND ND | 9240 ND |

To confirm our findings, we prepared selected batches of ASA and submitted the final lyophilized samples (500 mg/vial) to University of Minnesota for 2-D X-ray analysis, DSC and TGA. The submitted batches:

TABLE 19

Batch summary

| | Composition Details | |
|---|---|---|
| Batch No | ASA concentration | Bulk Solution for Lyophilization |
| Rho-11 | Plain API- | — |
| Rho11-121 | 100 mg/mL | TBA:WFI (80:20)-Qs |
| Rho11-125 | 100 mg/mL | TBA:WFI (75:25)-Qs |
| Rho11-126 | 100 mg/mL | TBA:WFI (65:35)-Qs |
| Rho11-127 | 75 mg/mL | TBA:WFI (65:35)-Qs |
| Rho11-134 | 50 mg/mL | TBA:WFI (65:35)-Qs |
| Rho11-139 | 50 mg/mL | Mannitol - 10 mg/ml Tween80 - 0.1 mg/ml TBA:WFI (65:35) |
| Rho11-140 | 50 mg/mL | Sucrose - 10 mg Tween80 - 0.1 mg TBA:WFI(65:35)-Qs |

Example 22

In this example, additional testing was done using:
a) 2D X-Ray Diffraction (2D XRD)

The D8 Discover 2D X-ray microdiffractometer is equipped with a two-dimensional Vantec detector, video camera/laser alignment system, and a Co $K_\alpha$ x-ray radiation point source ($\lambda$=1.79 Å), which is conditioned with a graphite monochromator. It is also equipped with point collimators of varying sizes and an x, y, z sample stage. Powder sample were mounted for reflection mode on sample holder and an 800 μm collimator was used. Measurement frames were scanned at 20/10° 2θ/ω respectively. Area detector images were finally converted to one-dimensional intensity vs. 2θ data sets by using an averaging integration algorithm. The 2 values are with respect to Co $K_\alpha$ radiation ($\lambda$=1.79 Å) and Cu $K_\alpha$ radiation ($\lambda$=1.54 Å).

b) Differential Scanning Calorimetry (DSC)

A differential scanning calorimeter (Q2000, TA Instruments, New Castle, DE) equipped with a refrigerated cooling accessory was used. Dry nitrogen gas was purged at 50 mL/min. The instrument was calibrated with indium. The powder samples were weighed and filled in an aluminum pan and sealed hermetically. The samples were cooled from RT to −10° C., equilibrated for 1 minute, and heated to 160° C. at 10° C./min.

c) Thermogravimetric Analysis (TGA)

A thermogravimetric analyzer (Q50, TA Instruments, New Castle, DE) was used. Dry nitrogen gas was purged at 50 mL/min during the measurement. The powder samples were filled in the aluminum pan. The samples were heated to 220° C. at 10° C./min.

Results

Thermal Analysis

The samples revealed pronounced weight loss around the melting temperature. Therefore, aspirin is likely to melt with decomposition. The melting point of aspirin is reported to be 135° C. (pubchem.ncbi.nlm.nih.gov). The enthalpy of melting of aspirin is reported to be in a range of 162-172 J/g (webbook.nist.gov).

| Sample | Temperature at which 10% weight loss [° C.] was observed (by TGA) | Melting point (Peak temp) [° C.] (by DSC) | Enthalpy of fusion [J/g] |
|---|---|---|---|
| Rho_11 | 160.4 | 144.0 | 168.7 |
| Rho_11_121 | 139.6 | 139.3 | 171.4 |
| Rho_11_125 | 141.0 | 139.2 | 174.3 |
| Rho_11_126 | 144.9 | 140.2 | 172.5 |
| Rho_11_127 | 142.0 | 139.4 | 176.8 |
| Rho_11_134 | 142.7 | 137.3 | 174.3 |
| Rho_11_139 | 143.5 | 139.7 | 154.8 |
| Rho_11_140 | 142.0 | 136.3 | 168.7 |

XRD pattern of the lyophilized samples match with that of aspirin comparable with the reference diffraction patterns in the Powder Diffraction Files of the International Centre for Diffraction Data (ICDD).

Figure 2:
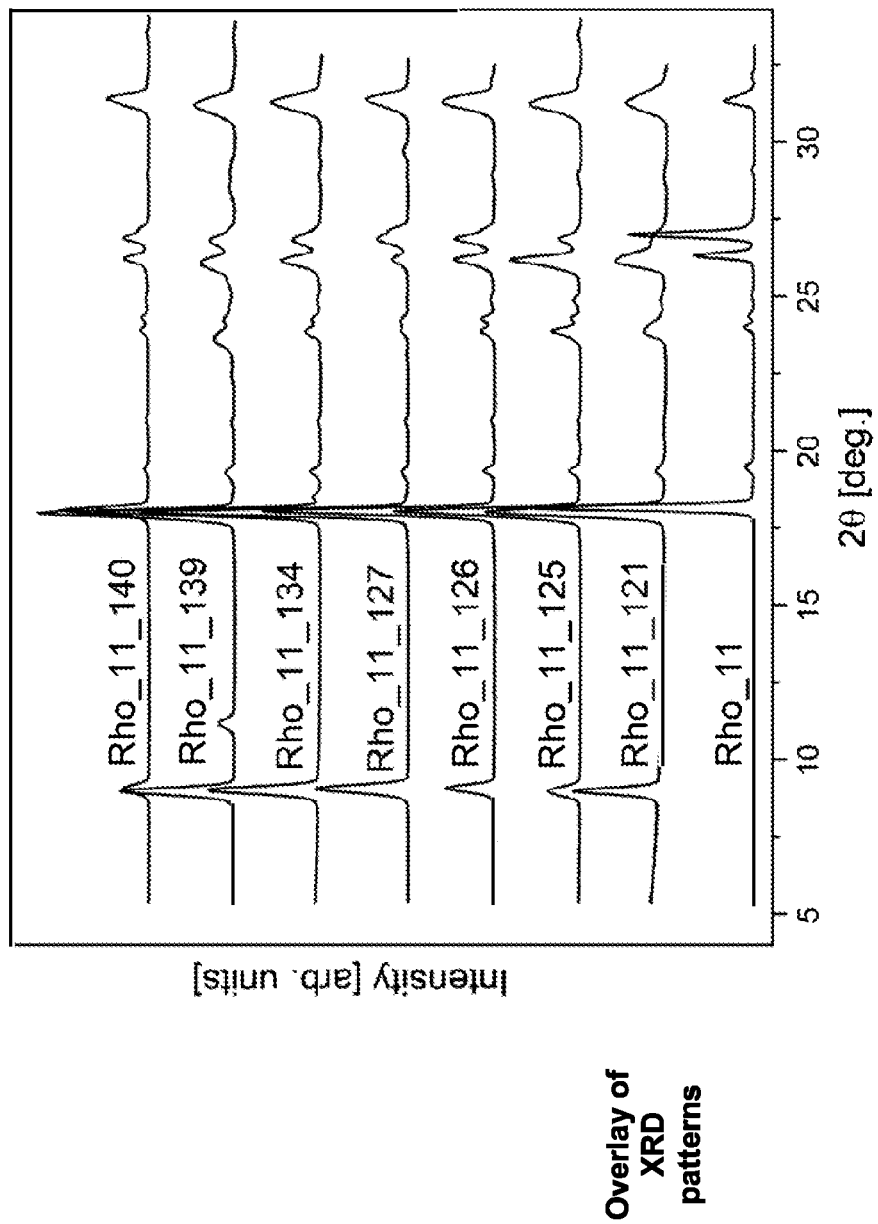
FIG. 2 is an overlay of XRD of tested samples in Example 21.

1. Aspirin melting point is approximately 135° C. and all the lyophilized samples show melting in the range of 136-140° C. Rho_11 shows a slightly higher melting temperature (144° C.).
2. Even though the melting enthalpy of lyophilized systems match with literature, enthalpy of melting is not a reliable parameter. 10% weight of loss (obtained from TGA) is observed at the melting point (obtained from DSC). There may be decomposition at the melting temperature.
3. The lyophilized systems show batch to batch consistency.
4. All the systems show crystalline behavior. See FIG. 2.

What I claim:

1. A lyophilized aspirin composition, comprising a lyophilized mixture of crystalline aspirin in free acid form, a bulking agent, and a surfactant, wherein the crystalline aspirin is characterized by a reflection X-ray powder diffraction pattern having a split peak at 2θ of 26.7°-26.9°.

2. A lyophilized aspirin composition, comprising a lyophilized mixture of crystalline aspirin in free acid form, a bulking agent, and a surfactant, wherein the crystalline aspirin is characterized by a reflection X-ray powder diffraction pattern having a peak at 2θ selected from the group consisting of 26.733°, 26.838° and 26.911°.

3. The lyophilized aspirin composition of claim 2, wherein the crystalline aspirin is characterized by a reflection X-ray powder diffraction pattern having peaks at 2θ of 7.573°, 12.000°, 15.382°, 16.532°, 20.443°, 22.426°, 24.777°, 26.733°, 32.385° and 39.073°.

4. The lyophilized aspirin composition of claim 2, wherein the crystalline aspirin is characterized by a reflection X-ray powder diffraction pattern having peaks at 2θ of 6.966°, 7.684°, 13.965°, 15.494°, 16.644°, 20.544°, 22.525°, 26.838°, 32.494° and 39.172°.

5. The lyophilized aspirin composition of claim 2, wherein the crystalline aspirin is characterized by a reflection X-ray powder diffraction pattern having peaks at 2θ of 6.939°, 7.683°, 13.934°, 15.463°, 22.488°, 26.911°, 31.284° and 37.286°.

6. The lyophilized aspirin composition of claim 1, wherein the crystalline aspirin has a melting point as determined by differential scanning calorimeter of from 136° C. to 144° C.

7. The lyophilized aspirin composition of claim 6, wherein the melting point is from 136° C. to 140° C.

8. The lyophilized aspirin composition of claim 6, wherein the melting point is 144° C.

9. The lyophilized aspirin composition of claim 2, wherein the crystalline aspirin is lyophilized from a solution containing aspirin, t-butyl alcohol and water.

10. The lyophilized aspirin composition of claim 9, wherein the ratio of t-butyl alcohol to water in the solution is about 80:20.

11. The lyophilized aspirin composition of claim 9, wherein the concentration of the aspirin in the solution is from about 50 mg/mL to about 100 mg/mL.

12. The lyophilized aspirin composition of claim 11, wherein the concentration of the aspirin in the solution is about 50 mg/mL.

13. The lyophilized aspirin composition of claim 11, wherein the concentration of the aspirin in the solution is about 75 mg/mL.

14. The lyophilized aspirin composition of claim 11, wherein the concentration of the aspirin in the solution is about 100 mg/mL.

15. The lyophilized aspirin composition of claim 1, wherein said composition comprises less than about 2.0% total degradation products after 2 years at 25° C.

16. The lyophilized aspirin composition of claim 1, wherein said composition comprises less than about 1.5% salicylic acid by weight after 2 years at 25° C.

17. The lyophilized aspirin composition of claim 1, wherein said composition comprises less than about 1.0% salicylic acid by weight after 2 years at 25° C.

18. The lyophilized aspirin composition of claim 1, wherein said bulking agent is selected from the group consisting of sucrose, lactose and mannitol.

19. The lyophilized aspirin composition of claim 18, wherein the bulking agent is mannitol.

20. The lyophilized aspirin composition of claim 1, wherein the surfactant is polysorbate 80.

* * * * *